United States Patent [19]

Coe et al.

[11] Patent Number: 5,540,936
[45] Date of Patent: Jul. 30, 1996

[54] METHOD OF PRODUCING LIPOSOMES

[75] Inventors: Royden M. Coe, Bordentown; Laura Edgerly-Pflug, Spotswood; Lawrence Boni, Monmouth Junction, all of N.J.; Joel Portnoff, Richboro, Pa.; Sharma R. Minchey, Monmouth Junction, N.J.

[73] Assignee: The Liposome Company, Inc., Princeton, N.J.

[21] Appl. No.: 253,145

[22] Filed: Jun. 2, 1994

Related U.S. Application Data

[63] Continuation-in-part of Ser. No. 41,780, Apr. 2, 1993, abandoned.

[51] Int. Cl.$^6$ .................................................. A61K 9/127
[52] U.S. Cl. ............................ 424/450; 264/4.1; 264/4.3; 428/402.2
[58] Field of Search ...................... 424/450; 428/402.2; 264/4.1, 4.3

[56] References Cited

U.S. PATENT DOCUMENTS

| | | | |
|---|---|---|---|
| 4,460,577 | 7/1984 | Moro et al. | 424/180 |
| 4,522,803 | 6/1985 | Lenk et al. | 424/1.1 |
| 4,588,578 | 5/1986 | Fountain et al. | 424/1.1 |
| 4,746,516 | 5/1988 | Moro et al. | 424/450 |
| 4,781,871 | 11/1988 | West et al. | 264/43 |
| 4,861,580 | 8/1989 | Janoff et al. | 424/1.1 |
| 4,891,208 | 1/1990 | Janoff et al. | 424/1.1 |
| 4,897,384 | 1/1990 | Janoff et al. | 514/34 |
| 4,935,244 | 6/1990 | Clark | 424/450 |
| 4,975,282 | 12/1990 | Cullis et al. | 424/450 |
| 5,030,453 | 7/1991 | Lenk et al. | 424/450 |
| 5,041,278 | 8/1991 | Janoff et al. | 424/1.1 |
| 5,082,664 | 1/1992 | Lenk et al. | 424/450 |
| 5,100,662 | 3/1992 | Bolcsak et al. | 424/88 |
| 5,169,637 | 12/1992 | Lenk et al. | 424/450 |
| 5,211,955 | 5/1993 | Legros et al. | 424/450 |
| 5,230,899 | 7/1993 | Park | 424/450 |
| 5,234,635 | 8/1993 | Grollier et al. | 264/4.6 |

FOREIGN PATENT DOCUMENTS

| | | | |
|---|---|---|---|
| 2561101 | 9/1985 | France | A61K 9/00 |
| 88/03797 | 6/1988 | WIPO | A61K 9/66 |

OTHER PUBLICATIONS

Frøkjaer, et al., "Stability Testing of Liposomes During Storage", in: *Liposome Technology, vol. 1:Preparation of Liposomes*, (G. Gregoriadis, ed.), CRC Press, Boca Raton, FL(1984), pp. 235–245.

Metje, et al., "Herstellung und Vermessung von Liposomen", SOFW—Seifen, Ole, Fette, Wachse, 114(1988) 21, Apr., No. 7, Augsburg, DE.

*Primary Examiner*—Gollamudi S. Kishore
*Attorney, Agent, or Firm*—Kenneth B. Rubin

[57] ABSTRACT

This invention provides a process for the production of liposomes by combining an organic phase and an aqueous at a volume ratio of less than 3:1; the process can be conducted under conditions which obtain a single-modal population distribution of liposomes encompassing a pre-selected mean particle size. A novel intermediate product obtained during the process, which can itself be used for the topical delivery of a bioactive agent, is also provided.

17 Claims, 12 Drawing Sheets

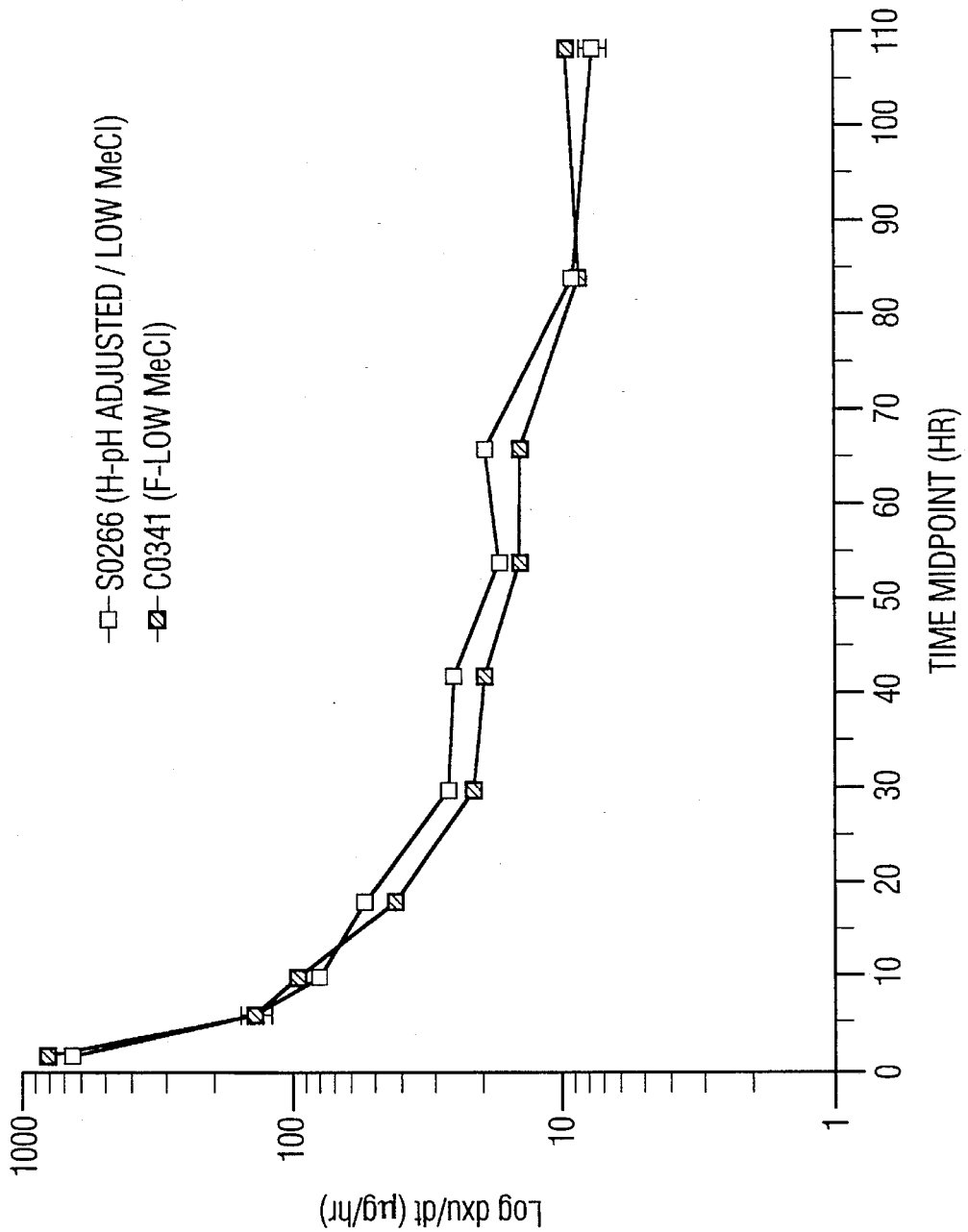

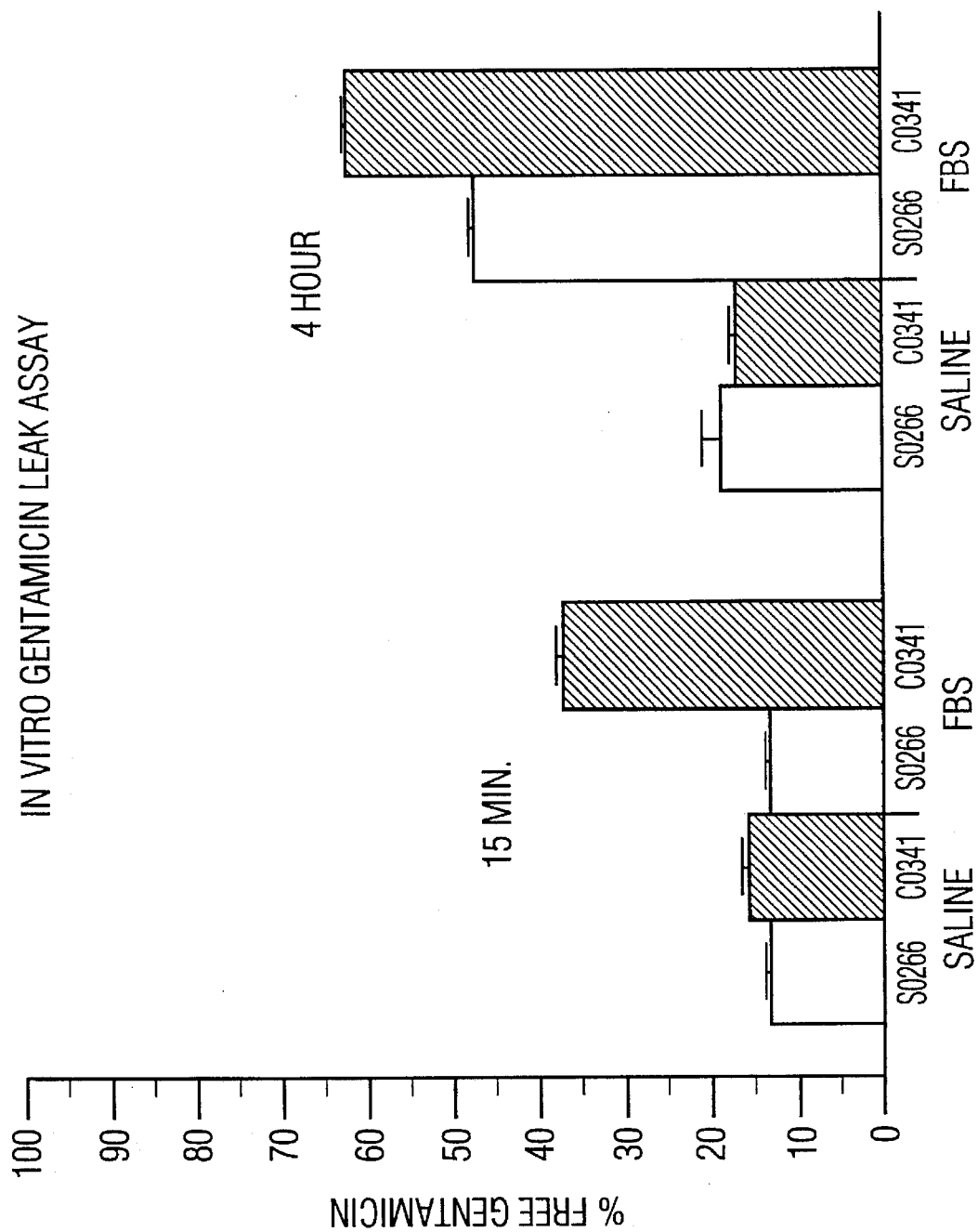

METHOD OF PRODUCING LIPOSOMES

This application is a continuation-in-part of U.S. Ser. No. 08/041,780, filed Apr. 2, 1993, now abandoned, the contents of which are incorporated herein by reference.

The present invention is directed to to a process of preparing liposomes which requires less solvent than in prior processes. A novel intermediate product made by the process of the present invention is also disclosed. The present invention is also directed to a method of producing liposomes in a two-phase system where the desired mean particle size of the liposomes is preselected and a favorable distribution of the desired mean particle size is obtained by selecting a suitable mixing speed, inert gas flow rate and reaction temperature.

Liposomes may be prepared by a two-phase mixing process using a water-immiscible organic phase and an aqueous phase. In this process, an amphipathic lipid or mixture of lipids is dissolved in an organic solvent which is not miscible with water, such as diethyl ether, methylene chloride, fluorinated hydrocarbons, mixtures thereof, and the like. To this solution is added an aqueous phase, such as water or water containing a dissolved salt or buffer, and an optional bioactive agent, such as a hydrophilic drug (e.g. gentamicin) which associates with the internal aqueous space of the liposome. Since the phospholipid bilayer formed during manufacture of the liposome acts as a barrier between the aqueous internal space and the outer aqueous environment, various water-soluble bioactive agents can be sequestered in the internal aqueous space. Lipophilic drugs (e.g. prostaglandin) can also be sequestered by associating with the hydrophobic portion of the liposome, in which case the lipophilic drug can be included in the organic phase.

The biphasic mixture is converted to liposomes by dispersing the aqueous phase within the organic phase while evaporating the organic solvent. Suitable evaporative techniques for removing the solvent include passing a stream of inert gas over or through the mixture, heating the mixture, or reducing the pressure above the mixture by vacuum.

In some prior practices, the volume of solvent used to dissolve the lipid often exceeds the aqueous volume by an amount sufficient to completely emulsify the aqueous material. For example, in some of the examples presented in U.S. Pat. No. 4,522,803, a minimum of 3 volumes of organic solvent to 1 volume of aqueous phase is used. The use of such relatively large amounts of solvent in the formation process can add significantly to the cost of producing liposomes. This is due to the cost of the solvent as well as the additional time needed to remove the solvent during processing. It would therefore be of benefit to devise a process for the production of liposomes which employs much lower concentrations of solvent.

In one method for the manufacture of liposomes, the organic and aqueous phases are combined in a reactor, typically equipped with a mixing assembly. The combined phases are mixed together under heating while the organic solvent is removed. This is typically accomplished by bubbling an inert gas (e.g. nitrogen gas) through the mixture, a procedure often referred to as sparging.

The resulting liposomes typically vary widely in size from relatively small liposomes (e.g. 100–200 nm) to very large liposomes (e.g. greater than 5000 nm). Thus, the mean particle size of the resulting liposome population can also vary widely from one batch to another. Accordingly, liposomes made using a water-immiscible organic solvent often have a distribution of particle sizes which vary over a wide range and may be multi-modal, that is, having more than one distinct population of diverse particle sizes.

In some applications, it is desirable to have a liposome population having a more narrow particle size range. In particular, it is desirable to have a single-modal population distribution where a significant percentage of the liposomes are of a similar size.

Conventionally, diverse liposome populations are converted to a single-modal population distribution by passing the liposomes several times through a filter of designated size. The pore size of the filter is approximately equal to the desired mean particle size. During the filtering procedure, some of the larger liposomes will be reduced in size as they pass through the filter, thereby increasing the population having approximately the desired mean particle size.

However, it often takes several passes through a filter to obtain a population of liposomes having the desired narrow particle-size distribution. The filtering procedure can thus be time consuming and add significantly to the cost of producing the liposomes.

It would therefore be a significant advance in the art to provide a process in which a liposome population can be obtained without extensive post-production filtering procedures, and particularly to a liposome population having a single-modal population distribution.

It would be a further advance in the art to provide a process of producing liposomes in which a mean particle size is selected and the process conducted in a manner which produces a single-modal population distribution encompassing the preselected mean particle size.

It is desirable for liposomes to be able to sequester an encapsulated agent from molecules as small as calcium ions for more than six months. The stability of entrapment of a bioactive agent by liposomes is measured by how much of the bioactive agent leaks out over a significant period of time. For example, when placed in a buffer containing isotonic saline at a neutral pH, liposomes containing a bioactive agent (e.g. a hydrophilic or lipophilic drug) should exhibit prolonged stability in storage.

There are at least two factors which can significantly affect the ability of a liposome to sequester its occluded space from the external environment over time. One factor is the presence of agents in the exterior environment which disrupt the bilayer organization such that while the lipids remain intact, the membrane develops a pore. The other factor is auto-oxidation of the lipids whereby the hydrocarbon chains of the lipids form peroxides which destabilize the bilayers. The rate of oxidation, and therefore the destabilization of the bilayers, can be reduced by the addition of antioxidants, such as butylated hydroxytoluene (BHT), to the liposome preparation.

The rate of auto-oxidation is also influenced by the pH of the medium used to produce liposomes. The pH of the processing medium in prior methods is generally in the range most compatible with the bioactive agent which is sequestered in the aqueous compartment of the liposome. However, some bioactive agents (e.g., gentamicin) typically exist in suspension at a pH range (e.g., 4.4–4.6) which adversely affects the lipid material causing the bilayers to destabilize.

It would therefore be a significant advance in the preparation of liposomes to conduct the process at a pH more compatible with the lipid bilayers so as to improve the stability of the liposomes by lowering the rate of auto-oxidation and thereby maintaining a high level of bioactive agent within the liposomes over an extended period of time.

SUMMARY OF THE INVENTION

The present invention is generally directed to a process for producing liposomes, which employs less solvent than previous methods. The process is premised on the discovery that it is not necessary to completely emulsify the aqueous phase within the organic phase. The combined phases can instead be in the form of a cloudy suspension and still be processed into liposomes. The volume ratio of solvent to aqueous phase in accordance with the present invention is broadly stated to be generally less than 3:1, preferably from about 0.2:1 to about 1.0:1. The combined phases can be processed at a pH within a range most compatible with the lipid material, preferably in the range of 5.5 to 7.5, most preferably at a pH of about 6.5 for most lipids. Preferably, the concentration of lipid in the combined aqueous and organic phases is at least about 10 mg/ml.

Preferably, the liposome produced is a multilamellar liposome comprising a solute entrapped in each of its aqueous compartments, wherein the concentration of the solute in each of the aqueous compartments is substantially equal, that is, is a multilamellar liposome having substantially equal interlamellar solute distribution.

During the processing of the combined phases, an intermediate product may be produced which is in the form of a viscous gel. The gel is comprised of lipid material which is in the process of forming lipid bilayers. This intermediate product may be used as a vehicle for the topical administration of a bioactive agent, such as an aminoglycoside antibiotic, or analogues or derivatives thereof, for the treatment and/or prevention of a variety of infections.

In another aspect of the invention, the process is generally directed to preparing liposomes having a single-modal population distribution encompassing a preselected mean particle size. The term "single-modal population distribution" as used herein shall mean that most of the liposomes have a particle size within a continuous range of particle sizes which encompasses the mean particle size. The term "mean particle size" shall mean the sum of the diameters of each liposome of the population divided by the total number of liposomes.

The mean particle size may be chosen before the manufacturing process commences and the process structured to produce a liposome population encompassing the mean particle size. Thus, the process of making liposomes, in accordance with this aspect of the invention, obtains a single-modal population distribution of liposomes which encompasses the preselected mean particle size. This process can greatly reduce or completely eliminate the need for post-production sizing procedures which are often required with this type of liposome production scheme.

This aspect of the present invention is premised on the discovery that three of the many variables in the described process for producing liposomes are highly influential in determining the size distribution of the liposomes produced by that process. These three principal variables are 1) the relative speed of the mixing apparatus; 2) the rate of flow of the inert gas to remove the solvent from the mixture of the organic and aqueous phases (that is, the sparge rate); and 3) the temperature of the mixture (that is, the reaction temperature). The present inventors have determined that there is a relationship between these three variables such that, by an appropriate selection of the variables, a liposome population having a single-modal population distribution encompassing a preselected mean particle size can be obtained.

The size distribution of the liposomes is generally affected by these three principal variables in the following manner. As the mixing speed or the temperature of the reaction is increased, the size of the liposomes will generally decrease. Conversely, as the sparge rate is increased, the size of the liposomes will generally increase. Accordingly, the process of the present invention for the production of liposomes in its broadest aspect comprises selecting a desired mean liposome size, combining an organic phase, composed of an amphipathic lipid in a water-immiscible solvent, with an aqueous phase which optionally may include a bioactive agent, and mixing the combined phases at a preselected mixing speed, sparge rate and reaction temperature in accordance with the desired mean particle size of the liposomes. In particular embodiments, the solvent to aqueous phase volume ratio of the components is less than 3:1, and the process is conducted at a pH in the range most compatible with the lipid material, typically 5.5 to 7.5.

The process of this invention can comprise associating a bioactive agent with the liposome produced. It will be understood by those skilled in the art that the bioactive agent (e.g. lipophilic and/or hydrophilic drugs) may be loaded into the liposomes either during the manufacture of the liposomes or after the liposomes have been formed. Preferably, the bioactive agent is a aminoglycoside antibiotic, including analogues, mixtures and derivatives thereof. Preferably, the aminoglycoside is selected from the group consisting of gentamicin, streptomycin, dihydrostreptomycin, tobramycin, neomycin, paromycin, ribostamycin, lividomycin, kanamycin, viomycin, sisomicin, netilmicin and amikacin. More preferably, the aminoglycoside is gentamicin.

The combined organic solvent and aqueous phases are processed in a reaction vessel under process conditions, including mixing speed, inert gas flow rate and reaction temperature sufficient to produce liposomes. The preselected mixing speed, sparge rate and reaction temperature may be chosen in accordance with the following equation:

$$y=B_0+B_1X_1+B_2X_2+B_3X_3+B_{12}X_1X_2+B_{13}X_1X_3+B_{23}X_2X_3+B_{11}X^2_1+B_{22}X^2_2+B_{33}X^2_3 \quad (1)$$

wherein:

$y$=the desired mean particle size $X_1$=the mixing speed $X_2$=the inert gas flow rate $X_3$=the reaction temperature $B_0$=a constant and $B_1$, $B_2$, $B_3$, $B_{12}$, $B_{13}$, $B_{23}$, $B_{11}$, $B_{22}$ and $B_{33}$ represent coefficients of regression in accordance with Table 1.

TABLE 1

| COEFFICIENT | FUNCTION |
| --- | --- |
| $B_0$ | Intercept |
| $B_1$ | Main effect of Mixing |
| $B_2$ | Main effect of Inert Gas Flow Rate |
| $B_3$ | Main effect of Reaction Temperature |
| $B_{12}$ | Two factor interaction between Mixing Speed and Inert Gas Flow Rate |
| $B_{13}$ | Two factor interaction between Mixing Speed and Reaction Temperature |
| $B_{23}$ | Two factor interaction between Inert Gas Flow Rate and Reaction Temperature |
| $B_{11}$ | Quadratic Effect of Mixing Speed |
| $B_{22}$ | Quadratic Effect of Inert Gas Flow Rate |
| $B_{33}$ | Quadratic Effect of Reaction Temperature |

Preferably, the inert gas flow rate is from about 0.4 liters/min to about 1.2 liters/min, the reaction temperature is from about 20 degrees C. to about 80 degrees C. and the mixing speed is in the range of up to about 2000 rpm. The process can also comprise: selecting a desired mean particle size for the liposomes; selecting values for eachj of the process conditions based upon the relationship of the process conditions in accordance with equation (1); determining a calculated mean particle size from equation (1) based upon the values selected in step (b); comparing the calculated mean particle size and the desired mean particle size, and, if these are sufficiently similar, then combining the aqueous and organic phase; and processing the combined aqueous phase and organic phase under the process conditions selected in step (b). If the calculated mean particle size and the desired mean particle size are not sufficiently similar, a new calculated mean particle size can be obtained, by varying at least one of the process conditions specified in Equation (1), while holding constant the remaining conditions, until a sufficiently similar new calculated mean particle size is obtained. Preferably, the inert gas flow rate is varied, while the mixing speed and the reaction temperature are maintained at constant levels; However, if the calculated and desired mean particle sizes are still not sufficiently similar, the inert gas flow rate and the mixing speed are both preferably varied while the reaction temperature remains constant. Preferably, the organic phase to aqueous phase ratio (volume/volume) is from about 0.2:1 to about 1.0:1, and the pH of the combined aqueous phase and organic phase is from about 5.5 to about 7.5.

The liposome produced under these process conditions is preferably a multilamellar liposome comprising a solute entrapped in each of its aqueous compartments, wherein the concentration of the solute in each of the aqueous compartments is substantially equal. A bioactive agent, which is most preferably the aminoglycoside antibiotic gentamicin, can be associated with the liposome. This invention also provides the liposome produced by the process provided herein.

The process can be terminated during the processing in the reaction vessel, at a point where the combined aqueous and organic phases have formed a viscous gel. A bioactive agent, preferably an aminoglycoside antibiotic, and most preferably, gentamicin, can be associated with this gel, either prior to, during, or after, its formation. The gel produced by such a process is also provided herein, and can be topically applied, using an amount of the gel containing an anti-infection effective amount of an antibiotic, to a warm-blooded animal, preferably, a human, to treat or prevent an infection in the animal. Preferably, the antibotic is gentamicin.

Further provided herein is a storage-stable liposome which comprises a bioactive agent, a lipid bilayer comprising a lipid and a compartment comprising an aqueous solution having a stability enhancing pH, wherein the lipid is a substantially pure lipid. Preferably, the liposome is a multilamellar liposome; preferably, the multilamellar liposome comprises a solute entrapped in its aqueous compartments, wherein the concentration of the solute in each of the aqueous compartments is substantially equal. Presently, the preferred bioactive agent is an aminoglycoside antibiotic, which can be selected from the group consisting of gentamicin, amikacin, streptomycin, dihydrostreptomycin, tobramycin, neomycin, kanamycin, lividomycin, paromycin, ribostamycin, viomycin, sisomycin and netilmicin. More preferably, the aminoglycoside antibiotic is gentamicin, amikacin or tobramycin. Most preferably, presently, the aminoglycoside antibiotic is gentamicin.

Preferably, the substantially pure lipid is at least about 85% pure, more preferably, at least about 90% pure and most preferably, at least about 95% pure. Typically, the substantially pure lipid is substantially free of lysolipids. Preferably, less than about 5% of the lipid comprises lysolipid; more preferably, less than about 2% of the lipid comprises lysolipid. Preferably, the substantially pure lipid comprises a phospholipid, which is preferably egg phosdphatidylcholine (EPC). Typically, the ratio (w/w) of bioactive agent to lipid in the storage-stable liposome of this invention is at least about 1:20; desirably, the ratio (w/w) of bioactive agent to lipid is from about 1:5 to about 1:15, more desirably, the ratio of bioactive agent to lipid is about 1:10.

Typically, the aqueous solution in the storage-stable liposome is a saline solution. Desirably, the stability-enhancing pH of the aqueous solution is from about pH 5.5 to about pH 7.5. More desirably, presently, the stability enhancing pH is about 6.5.

Accordingly, in a preferred embodiment of the invention, the storage-stable liposome comprises an aminoglycoside antibiotic, substantially pure egg phosphatidylcholine and an aqueous saline solution of pH about 6.5, wherein the liposome is a multilamellar liposome comprising a solute entrapped in its aqueous compartments and the concentration of the solute in each of the compartments of the multilamellar liposome is substantially equal, wherein the egg phosphatidylcholine is at least about 85% pure and is substantially free of lysolipid, and wherein the ratio (w/w) of gentamicin to EPC is from about 1:15 to about 1:5. Preferably, the aminoglycoside antibiotic is gentamicin, amikacin or tobramycin. More prferably, the aminoglycoside antibiotic is gentamicin.

BRIEF DESCRIPTION OF THE DRAWINGS

FIG. 12. Gentamicin Urinary Excretion Rate vs. Time at Midpoint.

FIG. 13. In Vitro Gentamicin Leak Assay.

DETAILED DESCRIPTION OF THE INVENTION

Figure 1:
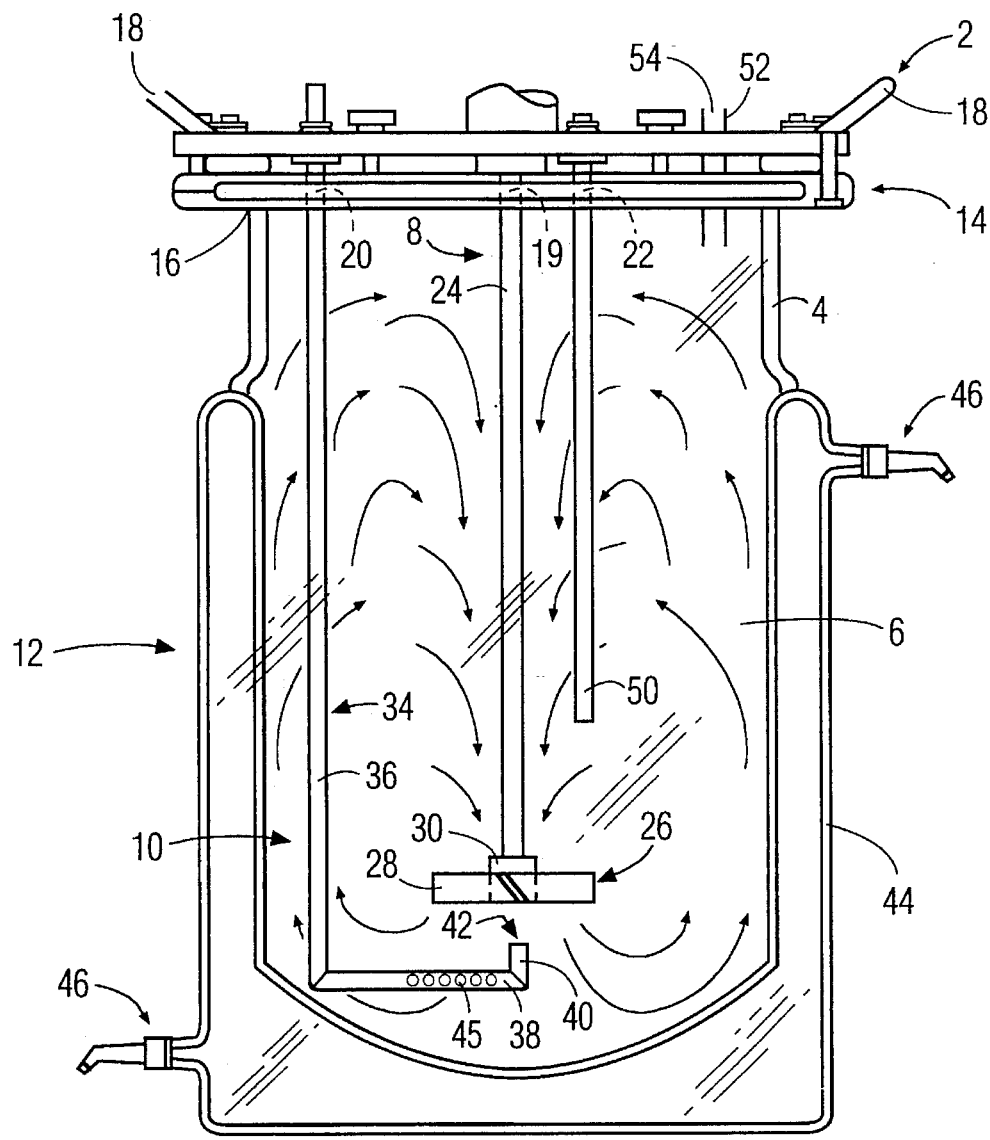
FIG. 1. Perspective View of a Vessel for Forming Liposomes.

In accordance with the present invention, a multilamellar liposome is formed based on a preselected mean particle size using less solvent and more favorable pH conditions than in prior methods. The process of this invention involves combining an organic phase and an aqueous phase, in a ratio of organic phase to aqueous phase (volume/volume) of less than about 3:1, and preferably with a volume ratio of less than about 1:1, so as to form a biphasic mixture. It is desirable that the least amount of organic solvent be used, to facilitate its removal. However, a minimum volume ratio of about 0.13:1 was found to be needed to achieve adequate drug entrapment, with a minimum ratio of 0.20:1 being preferred. In general, the minimum amount of organic solvent is used which can produce the desired liposome product. As a result of using less solvent than previously described methods, the overall volume of inert gas employed and the length of time of the sparging operation may be reduced.

The biphasic mixture is then processed under conditions sufficient to produce the liposome. The pH of the aqueous solution can be adjusted to a pH compatible with the one or more lipids used to prepare the liposome. "Compatible" is used herein to refer to an aqueous solution's pH which, when the solution is entrapped in the liposome and the liposome is stored for an extended period of time, results in minimization of lipid oxidation. Typically, the pH of the aqueous phase is from about 5.5 to about 7.5, preferably, about 6.5. The pH of the aqueous phase can be maintained within the desired range by adding appropriate amounts of pH adjusters including bases and acids, such as sodium hydroxide and hydrochloric acid, respectively.

Preferably, the multilamellar liposome comprises a solute entrapped in its aqueous compartments, wherein the concentration of the solute in each of the aqueous compartments is substantially equal, i.e., the multilamellar liposome has substantially equal interlamellar solute distribution. It has been found that preparation of such liposomes does not require the complete dispersion of the aqueous phase within the organic. These liposomes have less osmotic stress between their aqueous compartments than do "ordinary" multilamellar liposomes, i.e., liposomes which do not have substantially equal interlamellar solute distribution, and are therefore generally more stable.

The lipid materials used in the present invention are amphipathic in character. Hydrophilic character is imparted to the molecule through the presence of phosphato, carboxylic, sulphato, amino, sulfhydryl, nitro, and other like groups. Hydrophobicity is conferred by the inclusion of groups that are preferably long-chain saturated and unsaturated aliphatic hydrocarbon groups, but can also be such groups substituted by one or more aromatic, cycloaliphatic or heterocyclic groups. The preferred amphipathic compounds are phosphoglycerides such as phosphatidylcholines, phosphatidylethanolamines, lysophosphatidylcholines, lysophosphatidylethanolamines, phosphatidylserines, phosphatidylinositols, phosphatidic acids, phosphatidylglycerols and the like. Synthetic saturated compounds such as dimyristoyl phosphatidylcholine, dipalmitoyl phosphatidylcholine or distearoyl phosphatidylcholine, unsaturated species, such as dioleoyl phosphatidylcholine or dilinoleoyl phosphatidylcholine can be used. Glycolipids and glycosphingolipids, for example, can also be used.

A variety of cholesterols and other sterols and their water-soluble derivatives can be used to form liposomes (see, for example, U.S. Pat. Nos. 4,891,208 and 5,100,569, both incorporated herein by reference). Preferred of this group are cholesterol hemisuccinate, as discussed in U.S. Pat. No. 4,891,208. Certain water-soluble tocopherol derivatives, such as tocopherol hemisuccinate, can also be used to form liposomes, as discussed in U.S. Pat. No. 5,041,278.

The "aqueous phase" is a water-based mixture which may contain water-soluble components in solution, such as hydrophilic bioactive agents, as well as other components in suspension, or other forms of mixture. The "organic phase" is a mixture of a water-immiscible organic solvent which may contain components soluble in that solvent, such as lipophilic bioactive agents, as well as other components in suspension, or other forms of mixture. Generally the lipids used to form the liposomes are dissolved in the organic phase.

The solvents used to dissolve the lipid are generally immiscible with water. Such solvents include, but are not limited to, methylene chloride, chloroform, diethyl ether, fluorocarbons, chlorofluorocarbons, and the like.

The amount of lipid contained within the combined organic and aqueous phases may vary over a wide range, but is preferably at least 10 mg/ml, and more preferably at least 15 mg/ml. The more lipid material which is used, the greater the availability of lipid to entrap the aqueous phase. The amount of the lipid material in the combined organic/aqueous phase is also important in determining whether the combined phases will form a viscous gel intermediate.

Prior to conducting the liposome-forming process, a desired mean particle size is selected, typically depending on what agent is to be incorporated in the liposome or on the end use of the liposome. For example, when gentamicin is incorporated into the liposome, a typical mean particle size is about 200 nm. The components necessary to form the liposomes or the viscous gel intermediate are combined in the following manner. An amphipathic lipid or mixture of lipids is dissolved in a water-immiscible organic solvent to form an organic phase. After selecting the desired mean particle size, the organic phase is added to the aqueous phase. The mixture is then processed, typically in a reaction vessel, for example, a reaction vessel of the type, for example, shown in FIG. 1. Referring to FIG. 1, there is shown a processing system 2 including a vessel 4 defining a processing space 6 wherein the organic and aqueous phases are mixed together in accordance with the invention. The vessel is provided with a mixing system 8, a sparge system 10 and a heating/cooling system 12.

The vessel 4 defines the processing space 6 in which the aqueous and organic phases needed to form the liposomes will be combined, and the actual processing of the components into the liposomes or the viscous gel intermediate will take place. The vessel should be made of materials which will not readily adsorb the aqueous and organic phases and which can be readily cleaned and sterilized. Suitable materials include glass and stainless steel.

The vessel 4 is equipped with a cover 14 which is adapted to be placed in sealing engagement with a rim 16 of the vessel 4. The cover has opposed handles 18 to facilitate engaging and disengaging the cover 14 to the vessel 4.

The cover 14 is also provided with openings 19 and 20, respectively, for suspending the mixing system 8 and the sparge system 10 within the vessel 4. Another opening 22 is adapted to suspend a heat measuring means, such as a thermowell 50, to monitor the reaction temperature within the processing space 6.

The mixing system 8 includes a shaft 24 suspended in the processing space 6 through the opening 19 of the cover 14. The shaft 24 is operatively connected to a motor (not shown). The motor is capable of providing sufficient power to the shaft so that it may be rotated at a desired speed in accordance with the invention.

Operatively connected to the bottom portion of the shaft 24 is a mixing impeller 26. The impeller is rotated by the shaft and thereby mixes the aqueous and organic phases to a degree necessary to form the desired liposomes. The mixing impeller 26 may have a variety of configurations such as different shaped blades or a different number of blades besides the specific configuration shown in FIGS. 1 and 2. Preferably, the impeller 26 generates an axial or radial flow to the contents of the vessel 4 so as to ensure complete mixing of the aqueous and organic phases. Other mixing devices, such as an anchor mixer having blades which extend closer to the vessel wall, may also be employed in the present invention.

Figure 2:
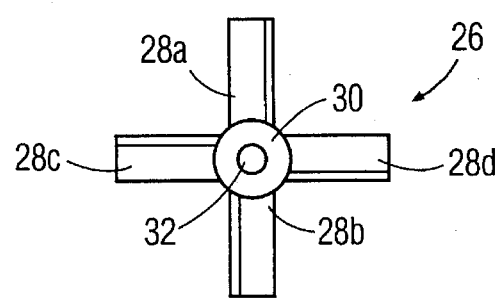
FIG. 2. Plan view of an impeller used in the vessel of FIG. 1.

The impeller 26, as best shown in FIG. 2, includes one or more pairs of opposed blades 28a–28d attached to a hub 30 which has an opening 32 for receiving the shaft 24. The impeller 26 is secured to and thereby rotatable by the shaft 24 by conventional means such as by a set screw (not shown) or the like.

The impeller shown specifically in FIG. 2 has two pairs of blades 28a, 28b and 28c, 28d. One or more of the blades 28 may be positioned parallel to the longitudinal axis of the shaft 24 or may be tilted at an angle. As shown in the embodiment of FIG. 2, each of the blades 28 is tilted at a 45° angle which facilitates passage of the blades through the contents of the vessel 4 and generates an axial flow of the vessel contents (as indicated by the arrows) shown in FIG. 1, particularly during the formation of the viscous gel (that is, the pre-liposome stage).

The blades 28a–28d may be set at more acute angles (that is, less than 45° as measured against the axis of the shaft 24) if desired. The more acute the angle the greater the resistance of the contents of the vessel against the impeller 26. This resistance can be readily overcome by increasing the torque of the shaft 24, such as by employing a motor capable of generating greater power. In addition, the change of angle can result in a change of the flow created by the impeller from an axial flow (45° angle) to a radial flow (parallel to the shaft). Because the impeller 26 is fixed to the shaft 24 the rotation of the shaft 24 causes the impeller blades 28 to rotate at the same rate of revolutions per minute.

The sparge system 10 shown in FIG. 1 includes a tube 34 connected at one end to an inert gas source (e.g. nitrogen gas, argon gas and the like, not shown). The tube 34 includes a central section 36 which extends downwardly to the bottom portion of the processing space 6. A tail section 38 of the tube extends perpendicular to the central section 36 toward the center of the bottom section of the processing space 6. In the embodiment shown in FIG. 1, the tail section 38 is provided with an upwardly extending nozzle 40 having one or more openings 42 for dispensing the inert gas in the form of discreet bubbles into the contents of the vessel. The tail section 38 of the tube 34 may be provided with one or more openings 45 for dispensing the inert gas in addition to or in place of the nozzle 40.

The bubbling of an inert gas into the contents of the vessel 4 facilitates removal of the organic solvent. The inert gas entraps the solvent and changes the vapor pressure within the vessel 4 so as to draw the volatile solvent out of the vessel through a tube 52 having an exit port 54.

The heating/cooling system 12 includes a jacket 44 for receiving a heated/cooled fluid (e.g. water) from a source (not shown) through a non-return valve 46. The jacket 44 circumscribes a substantial portion of the vessel 4 to provide controlled heating/cooling of the vessel contents. The fluid is removed from the jacket 44 via a non-return valve 48 and may be recirculated or discarded.

The temperature within the vessel may be measured using a customary thermowell 50 containing a thermometer, or preferably a thermocouple (not shown) connected to a display means (not shown). The thermocouple is a heat-sensitive probe which relays a signal corresponding to the reaction temperature which is then translated to an electrical signal which can be viewed on the display means such as a digital display screen. The temperature of the fluid supplied to the heating/cooling system is selected based on the desired reaction temperature.

The reaction vessel is operated by selecting processing conditions, particularly, mixing speed, sparge rate and temperature, which will provide the desired preselected mean particle size. For the apparatus shown in FIGS. 1 and 2, the mixing speed is the rate of revolution of the impeller 26 and corresponds to the number of revolutions per minute (rpm) of the shaft 24. The sparge rate is defined as the volume of the inert gas bubbled into the contents of the vessel per unit time, typically measured in liters/minute. The vessel temperature is, as shown FIG. 1, the temperature within the processing space 6 as measured by the thermowell 50.

Once values for each of the variables are chosen, the mean particle size is calculated using Equation (1):

$$y=B_0+B_1X_1+B_2X_2+B_3X_3+B_{12}X_1X_2+B_{13}X_1X_3+B_{23}X_2X_3+B_{11}X^2_1+B_{22}X^2_2+B_{33}X^2_3 \quad (1)$$

wherein:

y=the desired mean particle size $X_1$=the mixing speed $X_2$=the inert gas flow rate $X_3$=the reaction temperature $B_0$=a constant and $B_1$, $B_2$, $B_3$, $B_{12}$, $B_{13}$, $B_{23}$, $B_{11}$, $B_{22}$ and $B_{33}$ represent coefficients of regression in accordance with Table 1.

TABLE 1

| COEFFICIENT | FUNCTION |
| --- | --- |
| $B_0$ | Intercept |
| $B_1$ | Main effect of Mixing |
| $B_2$ | Main effect of Inert Gas Flow Rate |
| $B_3$ | Main effect of Reaction Temperature |
| $B_{12}$ | Two factor interaction between Mixing Speed and Inert Gas Flow Rate |
| $B_{13}$ | Two factor interaction between Mixing Speed and Reaction Temperature |
| $B_{23}$ | Two factor interaction between Inert Gas Flow Rate and Reaction Temperature |
| $B_{11}$ | Quadratic Effect of Mixing Speed |
| $B_{22}$ | Quadratic Effect of Inert Gas Flow Rate |
| $B_{33}$ | Quadratic Effect of Reaction Temperature |

Preferably, the inert gas flow rate is from about 0.4 liters/rain to about 1.2 liters/min, the reaction temperature is from about 20 degrees C. to about 80 degrees C. and the mixing speed is in the range of up to about 2000 rpm.

The selected mean particle size is compared to the desired mean particle size. If the calculated value and desired value are the same or sufficiently similar, then the processing system is operated at the selected values for the principal variables. "Sufficient similarity" is a degree of similarity, or correspondence, determined according to factors including but not limited to, the end use of the liposome, well within the purview of the ordinarily skilled artisan to choose given the teachings of this invention. If calculated and desired mean particle size are not sufficiently similar, then an adjustment is made to at least one of the principal variables. This can be accomplished by changing one of the variables within a selected range, while the other variables are held constant. The range of change is determined by the limits of the process and apparatus used in connection therewith.

In a preferred method of the invention, the reaction temperature and mixing speed are initially held constant while the sparge rate is changed, and that value entered into Equation (1). If a second variable must be changed, it is preferred to keep the reaction temperature constant while varying the mixing speed. However, the mixing system is typically limited by a maximum mixing speed. Accordingly, if a change in mixing speed approaches the maximum limits of the mixing system without achieving the desired degree of similarity between the calculated and desired mean particle sizes, then the reaction temperature may be changed. The changing of variables continues until the calculated mean particle size is the same as, or similar to, the desired mean particle size.

Once the desired mean particle size has been calculated, the aqueous and organic phases are combined so as to form a biphasic mixture. For example, the process can be conducted as follows, based on the use of a three liter reaction vessel. It should be understood that routine variations may be made to the ranges of the principal variables, if larger or smaller reaction vessels are used. The aqueous phase (e.g., a citrate buffer solution) with or without an optional bioactive agent is added to the reactor vessel. The mixing apparatus is activated at the preselected mixing speed typically in the range of up to 2,000 rpm. The organic phase comprised of a lipid (e.g., egg phosphatidylcholine and cholesterol) dissolved in an organic solvent (e.g., methylene chloride) is added to the aqueous phase under stirring by the mixing apparatus. Inert gas is sent through the tube 34 and bubbled into the reactor vessel at the preselected sparge rate typically from about 0.04 to 1.2 liters/minute. Once sparging is commenced, the temperature of the reactor vessel is typically raised to 20 to 80° C. by passing heated water through the jacket 44. It should be understood, however, that cooler temperatures may be used by passing cooled water through the jacket 44.

The process of this invention can comprise the step of associating a bioactive agent with the multilamellar liposome. A "bioactive agent" is a compound or composition of matter having some biological activity in an animal, or on an animal's cells in vitro. Bioactive agents include, but are not limited to: nucleic acids, polynucleotides, antibacterial compounds, antibiotics, antiviral compounds, antifungal compounds, antiparasitic compounds, tumoricidal compounds, proteins, toxins, enzymes, hormones, neurotransmitters, glycoproteins, immunoglobulins, immunomodulators, dyes, radio labels, radio-opaque compounds, fluorescent compounds, polysaccharides, cell receptor binding molecules, anti-inflammatories, antiglaucomic agents, mydriatic compounds, local anesthetics, and the like (see, for example, Lenk et al., U.S. Pat. No. 4,522,803; Fountain et al., U.S. Pat. No. 4,588,578; Janoff et al., U.S. Pat. Nos. 4,861,580 and 4,897,384; and Lenk et al., U.S. Pat. No. 5,082,664; each of which is incorporated herein by reference). "Association" as used herein described the entrapment of a bioactive agent in an aqueous compartment of the liposome, or association with the inner or outer surface of a lipid bilayer.

A viscous gel intermediate product may be produced in accordance with the process of the present invention. In the process, a cloudy lipid suspension is typically produced as the organic and aqueous phases are combined, and before the solvent is removed. Before sufficient solvent is removed for liposomes to form, and when the amount of water associated with the lipid material is still too low for liposomes to form, but when sufficient solvent is removed such that there is an excess of lipid over that which can be dissolved in the amount of solvent remaining, the lipids are typically organized in ill-defined bilayers, in the form of a gel. The resulting viscous gel is a reliable precursor of liposomes.

The formation of the viscous gel occurs when the organic and aqueous phases are combined at a volume ratio of less than 3:1. It has been found that the viscous gel readily forms at a volume ratio as low as about 0.13:1. Below about a 0.13:1 volume ratio, the lipid material tends to form spherical globules which must be specially processed to form the viscous gel, or the gel may not form at all. For example, the globules may be treated by elevating the mixing speed in order to break apart the globules. While the viscous gel can be formed at volume ratios of less than about 0.13:1, it is desirable to employ an organic to aqueous volume ratio of at least 0.13:1, preferably from about 0.2:1 to 1:1.

If a bioactive agent is added to the organic or aqueous phases prior to or during processing, the viscous gel will associate with the bioactive agent. The viscous gel, because of its characteristic ill-defined lipid bilayers, will entrap some of the bioactive agent, while some of the bioactive agent will remain associated with but not entrapped by the lipid material. This condition shall be referred to herein as "gel-associated" and means that the bioactive agent is part of the gel, including but not limited to, being adsorbed to the outer surface of the liposome or encapsulated within an aqueous or lipid portion of the liposome. This presents a desirable product for the topical administration of a bioactive agent for the treatment of infection.

Figure 3:
FIG. 3. Electron Micrograph of the Viscous Gel Intermediate.

An electron micrograph of a viscous gel produced in accordance with the present invention is shown in FIG. 3. At the lower center of the micrograph is a series of concentric layers of lipid material representative of poorly hydrated lipid bilayers.

The viscous gel can be used in a method for treating or preventing an infection in a warm-blooded animal, especially a human, wherein the gel comprises an anti-infection effective amount of an antibiotic and the administration comprises topical administration. For example, the viscous gel can be applied to a wound, as by layering onto the wound. The wound can then be optionally closed, as by surgical procedures. Particularly suited for association with the viscous gel are aminoglycoside antibiotics such as gentamicin (including gentamicin $C_1$, $C_{1a}$ and $C_2$), streptomycin, dihydrostreptomycin, tobramycin, neomycin B, paromycin, ribostamycin, lividomycin, kanamycin (including kanamycin A and B), viomycin, sisomicin, netilmicin and amikacin, as well as analogues and derivatives thereof. Gentamicin is the preferred aminoglycoside for use in the present invention.

It is believed that when a wound becomes infected, there is a massive infiltration of neutrophils, macrophages, and other cells of the immune system to the site of the injury. These cell types secrete a variety of enzymes which will serve to break down the lipid material, causing the gel-associated aminoglycoside to be slowly released at the site of the wound. In addition, the infiltrating neutrophils and macrophages will engulf the viscous gel, causing the aminoglycoside to be released intracellularly, thereby aiding the immune system in fighting off the local infection. Because the viscous gel does not have the degree of structural organization of typical liposomes, the gel-associated bioactive agent will be more readily available to the wound site.

The mode of administration of the preparation may determine the sites and cells in the organism to which the compound will be delivered. The viscous gel can be administered alone, but will generally be administered in admixture with a pharmaceutical carrier, such as saline, selected with regard to the intended route of administration and standard pharmaceutical practice. The preparations of the present invention are administered topically to the site of a wound prior to closing the wound by ordinary surgical procedures. The viscous gel may be combined with additives such as a viscosity modifier (e.g., polysaccharides) to improve administration thereof. Other uses, depending upon the particular properties of the preparation, may be envisioned by those skilled in the art.

An "anti-infection effective amount of an antibiotic is a therapeutically effective amount of the antibiotic, that is, an amount sufficient to inhibit the establsihment, growth or spread of an infection, and thereby achieve a physical or physiological response. The effective amount of a given aminoglycoside will vary with the mode of the administration, the particularities of the recipient, the sensitivity of the target bacteria, and other factors well known in the art. The amount of the bioactive agent which is gel-associated depends in part on the solubility of the agent in the aqueous or organic phase. For example, gentamicin has a solubility in the aqueous phase of up to about 850 mg/ml.

For administration to humans in the curative treatment of disease states, the prescribing physician will ultimately determine the appropriate dosage for a given human subject, and this can be expected to vary according to the age, weight, and response of the individual as well as the nature and severity of the patient's disease. The dosage of the drug in the viscous gel will generally be about that employed for the free drug. In some cases, however, it may be necessary to administer doses outside these limits.

Further provided herein is a storage-stable liposome which comprises a bioactive agent, a lipid bilayer comprising a lipid and a compartment comprising an aqueous solution having a stability enhancing pH, wherein the lipid is a substantially pure lipid. A "storage stable" liposome is a liposome which can be stored for an extended period of time with minimal degradation of liposome structure or properties, including minimal lipid hydrolysis and oxidation, and minimal leakage of the liposome's contents, including leakage of bioactuve agents entrapped in, or associated with, the liposomes. The liposome is stable during storage for periods of time of up to two years or more; liposome storage is typically under refrigerated conditions of about 4–5 degrees Celsius, but can be under other conditions if necessary. It is believed that the pH of the aqueous solution used to form the storage-stable liposome, and which is entrapped in the resultant liposome, contributes to the stability of the liposome during storage, and the maintenace of substantial by inhibiting lipid hydrolysis and oxidation.

Preferably, the liposome is a multilamellar liposome; preferably, the multilamellar liposome comprises a solute entrapped in its aqueous compartments, wherein the concentration of the solute in each of the aqueous compartments is substantially equal, that is, the multilamellar liposome preferably has substantially equal interlamellar solute distribution. Such liposomes can be formed according to the procedures described in Lenk et al. (U.S. Pat. Nos. 4,522, 803, 5,030,453 and 5,169,63, Fountain et al. (U.S. Pat. No. 4,5885,578) and Cullis et al. (U.S. Pat. No. 4,975,282), the contents of which are incorporated herein by reference. Substantially equal interlamellar solute distribution confers enhanced stability on the multilamellar liposome because, it is believed, of the enhanced osmotic balance, and reduced osmotic stress, between aqueous compartments. "Ordinary" MLVs, that is, those without substantially equal interlamellar solute distribution, have greater osmotic stress between compartments, and hence, less stability.

The storage-stable liposome of this invention comprises a bioactive agent entrapped in, or associated with, the liposome. The bioactive agent, which is a compound or composition of matter having some biological activity in an animal, or on an animal's cells in vitro, includes, but is not limited to: nucleic acids, polynucleotides, antibacterial compounds, antibiotics, antiviral compounds, antifungal compounds, antiparasitic compounds, tumoricidal compounds, proteins, toxins, enzymes, hormones, neurotransmitters, glycoproteins, immunoglobulins, immunomodulators, dyes, radio labels, radio-opaque compounds, fluorescent compounds, polysaccharides, cell receptor binding molecules, anti-inflammatories, antiglaucomic agents, mydriatic compounds, local anesthetics, and the like (see, for example, Lenk et al., U.S. Pat. No. 4,522,803; Fountain et al., U.S. Pat. No. 4,588,578; Janoff et al., U.S. Pat. Nos. 4,861,580 and 4,897,384; and Lenk et al., U.S. Pat. No. 5,082,664; each of which is incorporated herein by reference). "Entrapment" and "association" as used herein describe the entrapment of a bioactive agent in an aqueous compartment of the liposome, or association with the inner or outer surface of a lipid bilayer. Presently, the preferred bioactive agent is an aminoglycoside antibiotic, which can be selected from the group consisting of gentamicin, amikacin, streptomycin, dihydrostreptomycin, tobramycin, neomycin, kanamycin, lividomycin, paromycin, ribostamycin, viomycin, sisomycin and netilmicin. In a preferred embodiment of this invention, the aminoglycoside antibiotic is gentamicin. In another preferred embodiment, the aminoglycoside antibiotic is amikacin. In another preferred embodiment, the aminoglycoside antibiotic is tobramycin.

A "substantially pure lipid," as used herein, is typically at least about 85% pure, that is, it the lipid is constituted of at least about 85% lipid, and at most about 15% of breakdown products of the lipid and of other lipids. Preferably, the substantially pure lipid is at least about 90% pure; more preferably, the substantially pure lipid is at least about 95% pure. Lipid purity can be determined by a variety of methods well known to ordinarily skilled artisans, and readily practiced by them without undue experimentation, such as high performance liquid chromatography using ultraviolet detection at 205 nm, thin layer chromatography of phospholipids using a phsophorous specific assay and high pressure or thin layer chromatography using flame ionization (see, for example, U.S. Ser. No. 08/212,323, filed Sep. 9, 1994, now pending which is a continuation of U.S. Ser. No. 07/512,557, filed Apr. 12, 1990; and S. Frøkjaer et al., "Stability Testing of Liposomes During Storage," in: Liposome Technology, Volume I: Preparation of Liposomes G. Gregoriadis ed.), CRC Press, Boca Raton, Fla. (1984), pp. 247–258, the contents of which are incorporated herein by reference).

Preferably, the substantially pure lipid is substantially free of lysolipid. Lysolipids are amphipathic lipids with a headgroup and a single acyl chain, and can be present in lipid bilayers as a result of the hydrolysis of diacyl lipids. Accordongly, the formation of lysolipids can be a measure of lipid, and hence liposome, stability. Lysolipids destabilize liposomes, because, it is believed, that lysolipids are more stable in gels and therefore tend to form gels. The formation of lysolipids from diacyl lipids in lipid bilayers can induce changes in bilayer properties such as their permeability. Accordingly, liposomal bilayers that are substantially free of lysolipids are generally more stable than bilayers which contain a significant proportion of such lipids. "Substantially free" of lysolipids means that less than about 5% of the lipid comprises lysolipid, and preferably, less than about 2% comprises lysolipid.

Preferably, the substantially pure lipid comprises a phospholipid, which is preferably egg phosdphatidylcholine (EPC). The lipid can also comprise other phospholipids, amphipathic lipids other than phospholipids, sterols, such as cholesterol, sterol derivatives such as cholesterol hemisuccinate (CHS) and alpha-tocopherol or its derivatives, amongst other types of lipids.

Substantial lipid purity is maintained in the storage-stable liposome during storage by inhibiting lipid degradation, including lipid hydrolysis and oxidation; it is believed that the pH of the aqueous solution entrapped by the liposome contributes to this inhibition of degradation. Lipid hydrolysis occurs when the bond between an amphipathic lipid's headgroup, for example, the ester bond between a phospholipid's headgroup, and one of its fatty acid chains is disrupted, resulting in formation of a lysolipid, that is, a lipid with a headgroup and one acyl chain instead of two. Thus, the formation of lysolipids is a measure of the chemical stability of phospholipids. Oxidations are reactions, initiated by factors such as heat and light, which use molecular oxygen to form free radicals. Lipid oxidation can disrupt the double bonds in unsaturated fatty acids, and thereby degrade the lipid. Lipid oxidation can be monitored by a variety of methods well known to ordinarily skilled artisans and readily practiced by them without undue experimentation. Lipid hydrolysis and oxidation can be assayed by measuring the initial purity of a liposome's lipid component, and by measuring the initial content of lysophospholipid and free fatty acids corresponding to the lipid used to prepare the liposome. Lipid purity, and lysophosphlipid and free fatty acid content, can then be measured after storage, and compared with the initial values to determine lipid oxidation. Methods for determining lipid purity, and lysophospholipid and free fatty acid content, in a liposome preparation are well known to ordinarily skilled artisans and can be practiced by them without undue experimentation.

"Minimal lipid hydrolysis" and "minimal lipid oxidation" mean that substantially all of the lipid used to form the storage-stable liposome remains intact during storage. Minimization of hydroylsis and oxidation means that the purity level of the lipid does not substantially decrease during storage, and that the lysophosholipid and free fatty acid contents do not significantly increase during storage. Typically, less than about 15% of the pure lipid in the storage-stable liposome is hydrolyzed or oxidized, desirably about 10% or less of the lipid is hydrolyzed or oxidized, and more desirably, less than about 5% is hydrolyzed or oxidized.

For example, liposomes can be formed in accordance with the procedures described below (see Examples section), using egg phosphatidylcholine (EPC) and an aqueous solution having a pH of about 6.5. In the resultant liposome, EPC purity is initially typically about 96.5% (see Tables 7–16, below), and the lysophosphatidylcholine content is about 0.4%. The EPC purity is about the same after storage of the liposome for one-half, one, one and one-half or two years, and the lysophospholipid content does not significantly increase.

Typically, at least about 75% of these storage-stable liposomes have sizes in the range of 1.2–9.6 microns; desirably, at least about 95% of the liposomes have sizes in this range. The proportion of liposomes having sizes greater than 9.6 microns is typically less than about 10% and, is desirably less than about 5%, more desirably about 2% or less. The proportion of liposomes having sizes less than about 1.2 microns is less than about 10%, and desirably, is less than about 5%. This size distribution is also maintained during liposome storage for periods of up to two or more years.

These storage-stable liposomes typically exhibit less leakage than do liposomes formed at a non-stability enhancing pH, and consequently, maintain entrapped in the liposome a greater percentage of the bioactive agent originally entrapped therein, or associated therewith. It is believed that bioactive agent leakage is minimized in the storage-stable liposomes by maintenance of bilayer integrity through minimization of lipid hydrolysis, oxidation and other lipid degradation. For example, liposomes formed in accordance with the above-described procedures using EPC, gentamicin and a pH of about 6.5 typically exhibit less than 15% free gentamicin, that is, less than about 15% of the amount of the gentamicin originally entrapped in the liposomes leaks during storage, and 85% or more of the gentamicin is maintained in the liposome during storage.

EPC-containing liposomes formed in an aqueous solution of pH about 4.5 generally had a similar EPC purity in the inital liposome preparation (see Tables 17–20, below). However, after storage for similar periods of time, these liposomes exhibited a decline in EPC purity, and a significant increase in lysophospholipid content. Furthermore, the proportion of liposomes having sizes of less than about 1.2 microns is greater in liposomes formed at this pH, and the proportion of liposomes having sizes between about 1.2 microns and about 9.6 microns is less, than for liposomes formed at the stability enhancing pH of about 6.5. Such liposomes also typically exhibit a greater percentage of bioactive agent leakage than do liposomes formed at a stability-enhancing pH, that is, less of the bioactive agent originally entrapped in, or associated with, the liposome remains therein after storage than is the case for liposomes formed with aqueous solutions having a stability enhancing pH.

Furthermore, based upon independent model evaluation, studies showed that the elimination half-life of the storage-stable liposome, that is the amount of time required for one-half of the liposomes to be eliminated, was significantly longer than for liposomes formed at a lower pH (about 4.5; for example, a population of the storage-stable liposome was found to have a circulatory half-life of about 5.04 +/−1.91 hours, as opposed to 4.10+/−1.15 hours, for the lower pH formulation. Also, the percentages of administered gentamicin excreted in urine were 81.58+/−10.96 and 76.16+/−11.81, respectively, for the lower pH liposomes and for the storage-stable liposome). Free plasma gentamicin levels were higher in the lower pH group than for the storage-stable liposome (Cmax and AUC last values were 115.67+/−51.42 micrograms/ml and 90.842+/−51.41 micrograms-hr/ml, and 57.31+/−29.00 and 44.39+/−6.778, respectively, for the lower pH and storage-stable liposomes). The gentamicin free fraction in the lower pH group was about twice that of the storage-stable liposome.

Accordingly, the storage-stable liposome can be stored for extended periods of time with minimal liposome degradation. It is therefore particularly useful in connection with liposomal formulations containing bioactive agents, and with the therapeutic administration of such formulations, because, for example, the formulations can be manufactured in bulk, stored and then safely distributed over an extended period. The formulations can be given to the treatment subject in a large amount, increments of which can then be safely used by the subject over an extended period of time.

Typically, the ratio (w/w) of bioactive agent to lipid in the storage-stable liposome of this invention is at least about 1:20; desirably, the ratio (w/w) of bioactive agent to lipid is from about 1:5 to about 1:15, more desirably, the ratio of bioactive agent to lipid is about 1:10. Typically, the aqueous solution in the storage-stable liposome is a saline solution, but can be other aqueous solutions having a stability-enhancing pH which are known to ordinarily skilled artisans to be suitable for use in connection with liposome formation, including aqueous buffers such as citric acid buffers.

A "stability-enhancing pH" describes the pH of an aqueous solution at which lipid degradation, including lipid hydrolysis and lipid oxidation, is inhibited. Desirably, the stability-enhancing pH of the aqueous solution used in the storage-stable liposome is from about pH 5.5 to about pH 7.5. More desirably, presently, the stability enhancing pH is about 6.5.

Accordingly, in a preferred embodiment of the invention, the storage-stable liposome comprises an aminoglycoside antibiotic, substantially pure egg phosphatidylcholine and an aqueous saline solution of pH about 6.5, wherein the liposome is a multilamellar liposome comprising a solute entrapped in its aqueous compartments and the concentration of the solute in each of the compartments of the multilamellar liposome is substantially equal, wherein the substantially pure egg phosphatidylcholine is at least about 85% pure and is substantially free of lysolipid, and wherein the ratio (w/w) of gentamicin to EPC is from about 1:15 to about 1:5. Preferably, the aminoglycoside antibiotic is gentamicin, amikacin or tobramycin; more preferably, the aminoglycoside antibiotic is gentamicin.

The following examples are illustrative of embodiments of the invention and are not intended to limit the invention as encompassed by the claims forming part of the application.

EXAMPLES

Example 1

850 g (300 mM) of a citrate buffer solution (pH 4) was placed into a three liter glass reactor vessel equipped with a magnetically coupled mixing assembly Model #P310 having a 3 inch Lightnin A-200 impeller attached to the bottom of a shaft, the rotation of which was controlled by a bench-top motor controller #Z510122R20, all sold by Applikon Dependable Instruments, Inc., Foster City, Calif. The reactor vessel had the configuration essentially corresponding to the reactor vessel shown in FIG. 1 herein. The mixing assembly was activated and the shaft rotated at 1,000 rpm to thereby rotate the impeller at the same rate.

68.6 g of egg phosphatidylcholine (EPC) and 27.6 g of cholesterol were added to a beaker. 191.8 g of methylene chloride were added and the lipid mixture stirred until dissolved. The volume ratio of the solvent to aqueous phase is. 18:1 and the amount of lipid is 117 mg/ml. The resulting organic phase was added to the reactor vessel.

Nitrogen gas was bubbled through the tube of a sparge assembly of the type shown in FIG. 1 at the rate of 0.04 liter/minute. Thereafter, the temperature of the reactor vessel was gradually raised to 30° C. by circulating hot water through the jacket.

After at least three hours, substantially all of the methylene chloride was removed by the nitrogen gas (less than 0.1% remained, i.e.<0.2 grams), and a liposome population formed in the reactor vessel. The liposomes were brought to 1000 ml volume with the same citrate buffer solution mentioned above.

The particle size of the resulting liposomes was measured in a conventional manner using a NICOMP Model 270 Submicron Particle Sizer for liposomes having a particle size of less than about 1200 nm and a Malvern 3600 E Laser Diffraction Particle Sizer for liposomes having a diameter of greater than about 1200 nm.

Examples 2–8

The experimental procedure identified in Example 1 was repeated for Examples 2–8 by varying the mixing speed, inert gas flow rate and reaction temperature, as indicated in Table 2. The mean particle size for each of Examples 1–8 was measured in the manner described previously, and the results are also shown in Table 2.

TABLE 2

| EXAMPLE | MIXING SPEED (RPM) | INERT FLOW RATE (L/min) | REACTION TEMPERATURE (Degrees C.) | MEAN PARTICLE SIZE nm* |
|---|---|---|---|---|
| 1 | 1000 | 0.04 | 30 | 245 |
| 2 | 2000 | 0.04 | 30 | 218 |
| 3 | 1000 | 0.8 | 30 | 2800 |
| 4 | 2000 | 0.8 | 30 | 247 |
| 5 | 1000 | 0.04 | 50 | 202 |
| 6 | 2000 | 0.04 | 50 | 200 |
| 7 | 1000 | 0.8 | 50 | 2635 |
| 8 | 2000 | 0.8 | 50 | 226 |

*The sum of the diameter of each liposome divided by the total number of liposomes.

As shown by a review of the data in Table 2, varying the mixing speed, inert gas flow rate (sparge rate) and/or reaction temperature will affect the mean particle size of the liposomes. A comparison of Examples 1 and 2 shows that, by increasing the mixing speed (from 1,000 to 2,000 rpm), while holding the sparge rate and reaction temperature constant, there is a decrease in the mean particle size. A comparison of Examples 1 and 3 shows that an increase in the sparge rate (from 0.04 to 0.8 L/min), while holding the mixing speed and reaction temperature constant, results in an increase in the size of the liposomes. If just the reaction temperature is increased (compare Examples 1 and 5), the size of the liposomes generally decreases.

Prior to the present invention, obtaining a liposome population of a desired mean particle size required extensive, costly and time-consuming filtering procedures. This is because the selection of those process variables which most affected particle size were chosen randomly. In accordance with the present invention, the principal variables which most affect particle size have been identified and a process developed in which values for the principal variables are chosen in a non-random manner. Equation (1) associates those principal variables and combinations thereof, as represented by the coefficients $B_0$ through $B_{33}$, which most affect the mean particle size (Y).

The data analysis for determining the coefficients $B_0$ through $B_{33}$ was accomplished using Design-Expert, a software package for response surface and mixture experiments by STAT-EASE, Inc. In order to obtain a good fit to the quadratic model proposed in Equation 1, a log 10 transformation of the mean particle size data from Examples 1–8 shown in Table 2 was obtained. The values of the coefficients are shown in Table 3.

TABLE 3

| COEFFICIENT | VALUE |
|---|---|
| $B_0$ | 2.413100 |
| $B_1$ | −0.286392 |

TABLE 3-continued

| COEFFICIENT | VALUE |
| --- | --- |
| $B_2$ | 0.299464 |
| $B_3$ | −0.023978 |
| $B_{12}$ | −0.258263 |
| $B_{13}$ | 0.004272 |
| $B_{23}$ | 0.007034 |
| $B_{11}$ | 0.185706 |
| $B_{22}$ | 0.053462 |
| $B_{33}$ | −0.009501 |

From the coefficients shown in Table 3, several trends may be observed. All of the terms with negative coefficients act to decrease the particle size with an increase in the factor (e.g. mixing speed). That is, when the factor is increased, the particle size of the liposomes will generally decrease. The opposite is true for the positive coefficients. The two largest negative coefficients are associated with the mixing speed ($B_1$) and the interaction between mixing speed and inert gas flow rate ($B_{12}$). The largest positive coefficient is associated with the inert flow rate ($B_2$). Also, there is a relatively large positive coefficient associated with the second order term for the mixing speed ($B_{11}$). This positive second order term means that as the mixing speed increases there will be a point where the mean particle size will begin increasing instead of decreasing due to the negative first order term ($B_1$). Second order terms for the inert gas flow rate and reaction temperature are also shown in Table 3.

Examples 9–16

The procedure and apparatus identified in Examples 1–8 were repeated utilizing the mixing speed, inert gas flow rate and reaction temperatures shown in Table 4. The data was incorporated into Equation (1) to obtain a predicted mean particle size. The actual particle size was determined in the same manner as described in connection with Examples 1–8. The conditions and the predicted and actual mean particle sizes are shown in Table 4.

Figure 4:
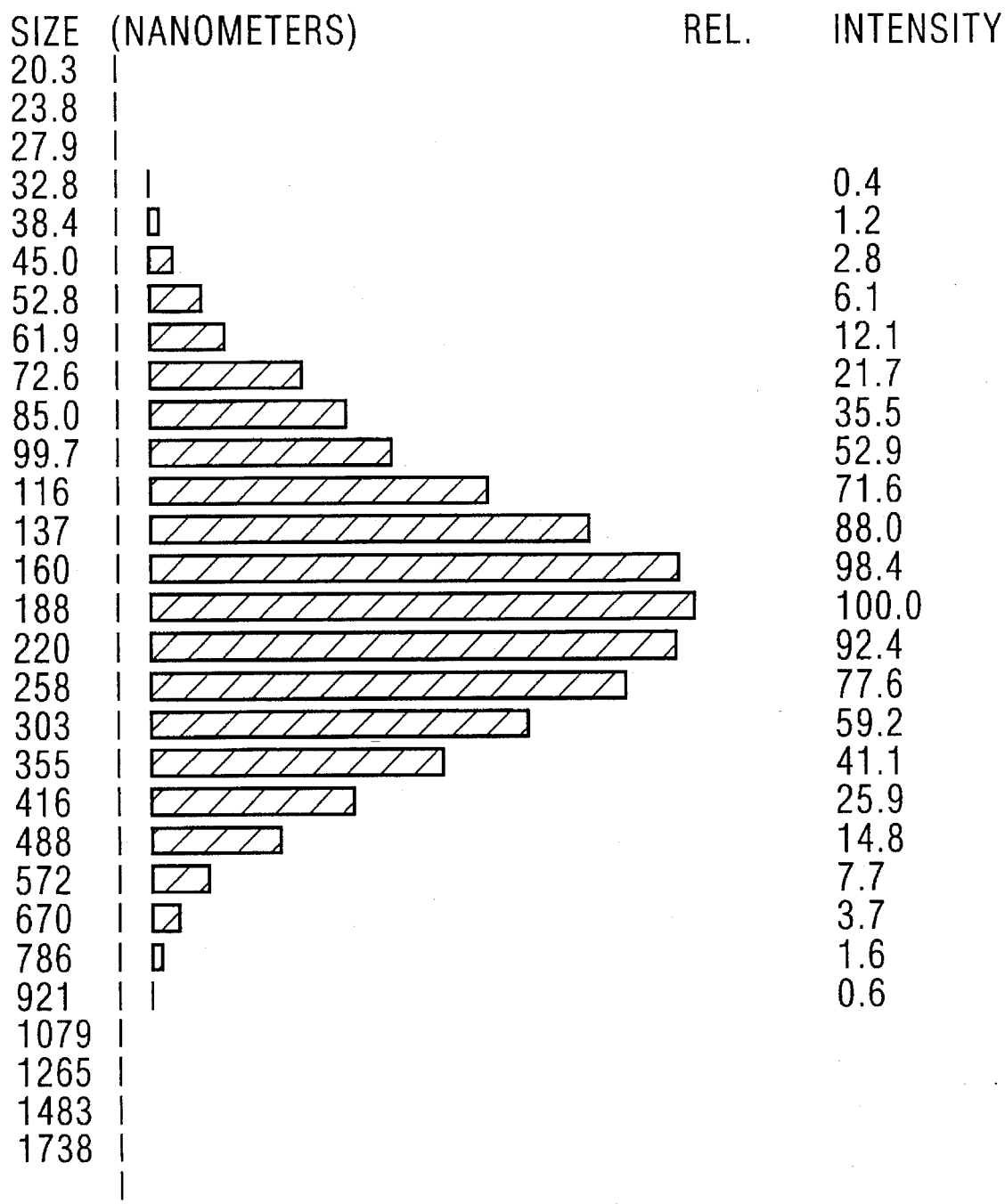
FIG. 4. Single-modal Size Distribution of Liposome Population.
Figure 5:
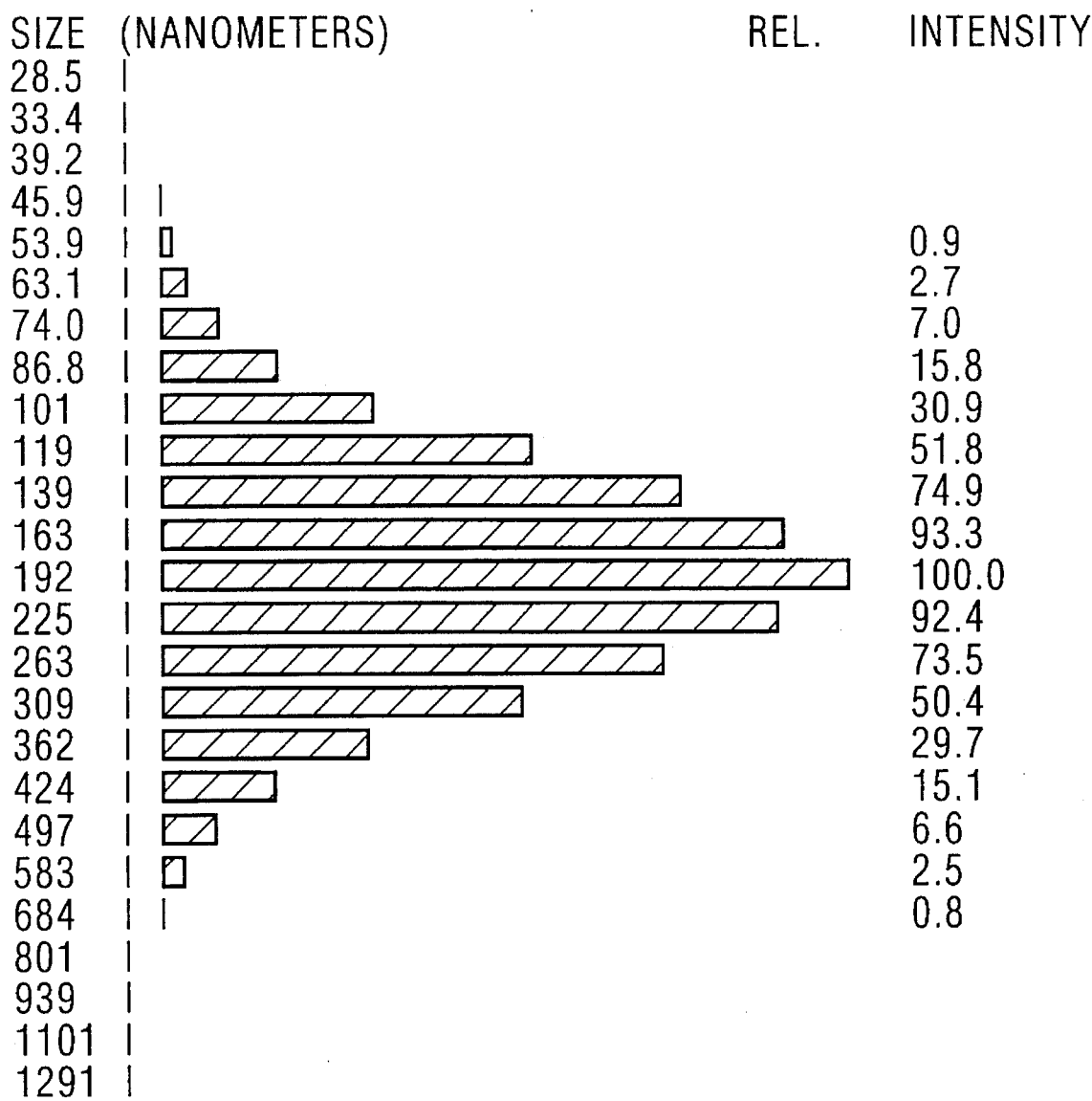
FIG. 5. Single-modal Size Distribution of Liposome Population.
Figure 6:
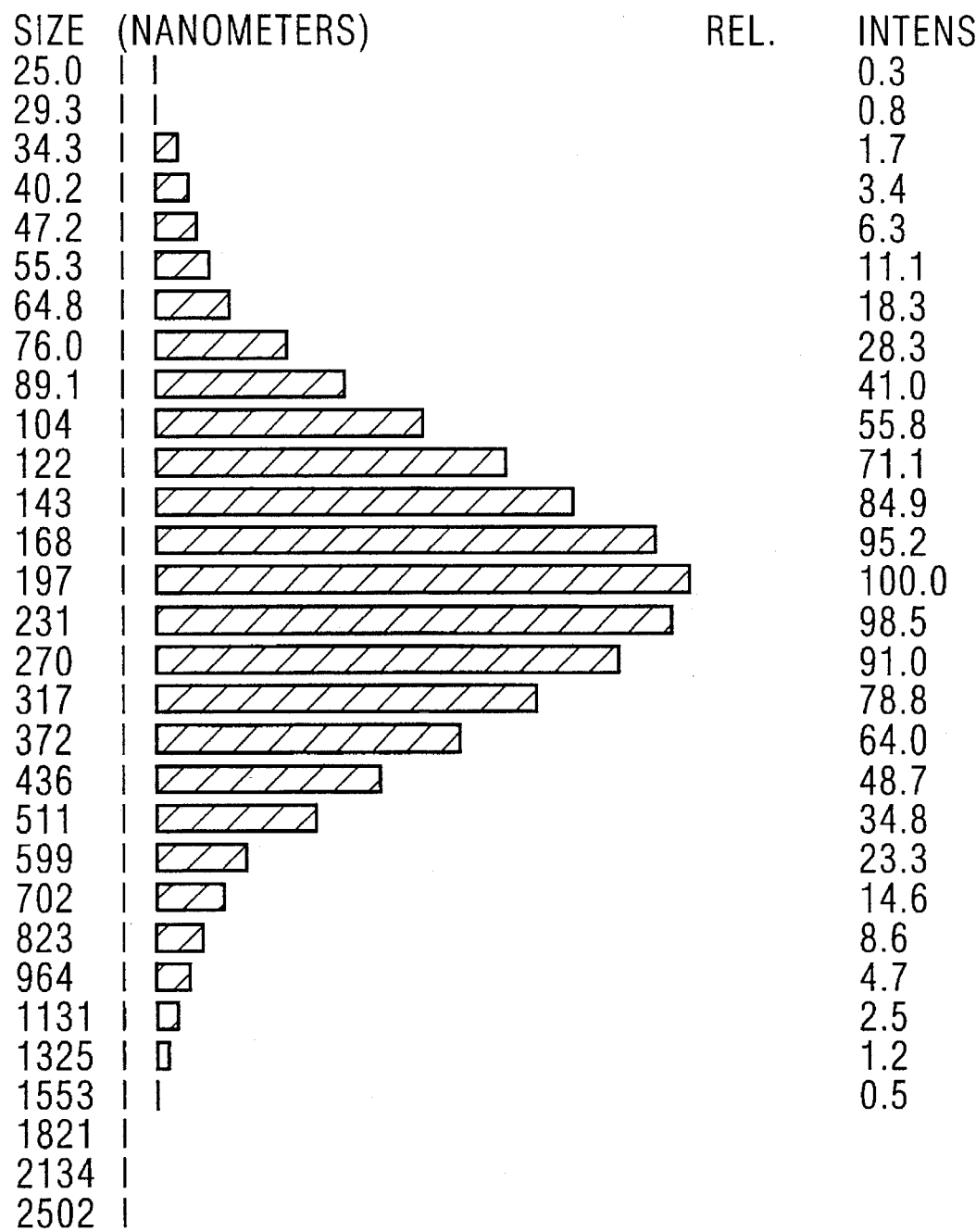
FIG. 6. Single-modal Size Distribution of Liposome Population.
Figure 7:
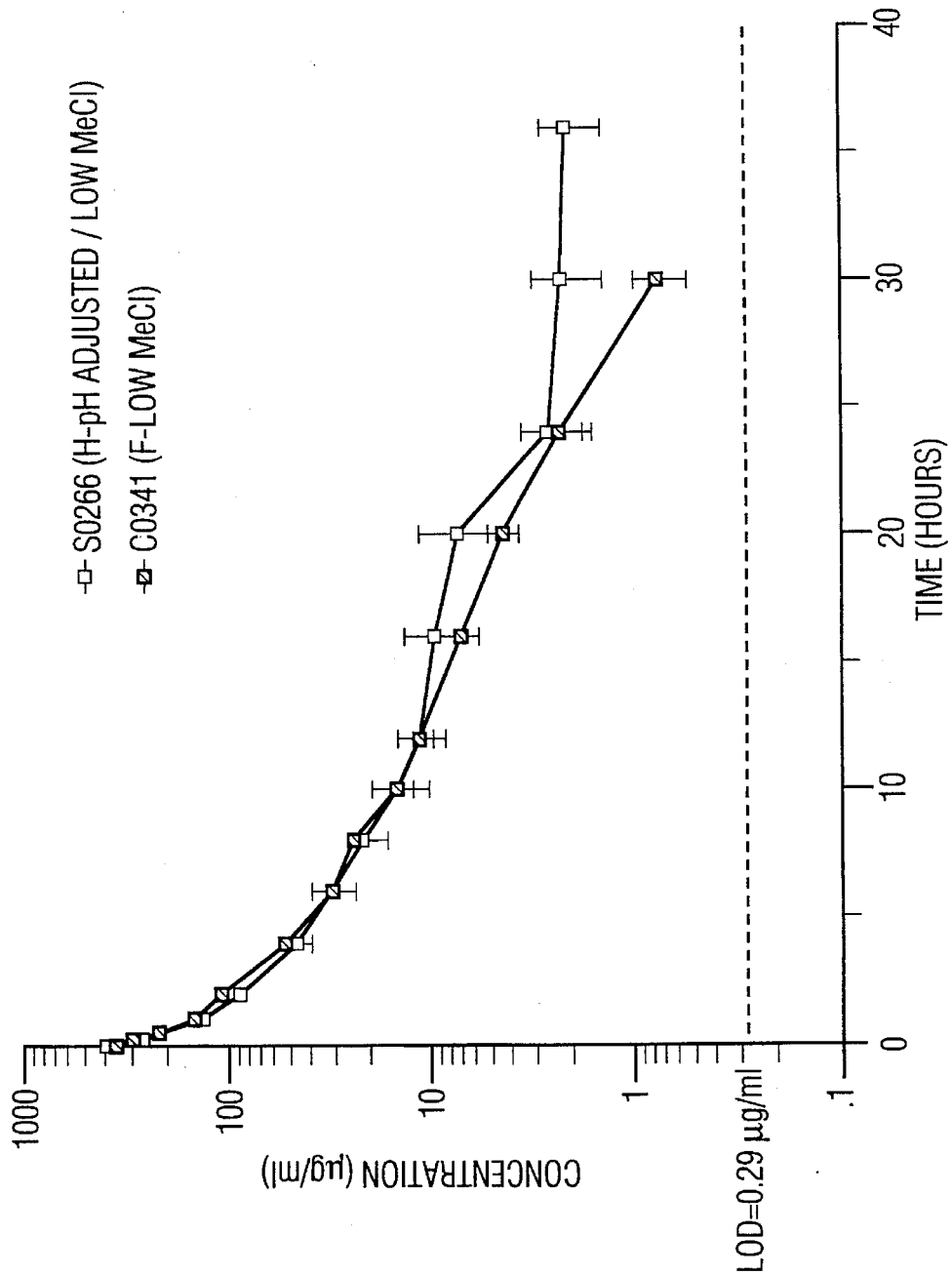
FIG. 7. Total Gentamicin Plasma Concentrations. Open squares: pH-adjusted (about pH 6.5); filled squares: lower pH formulation administered.
Figure 8:
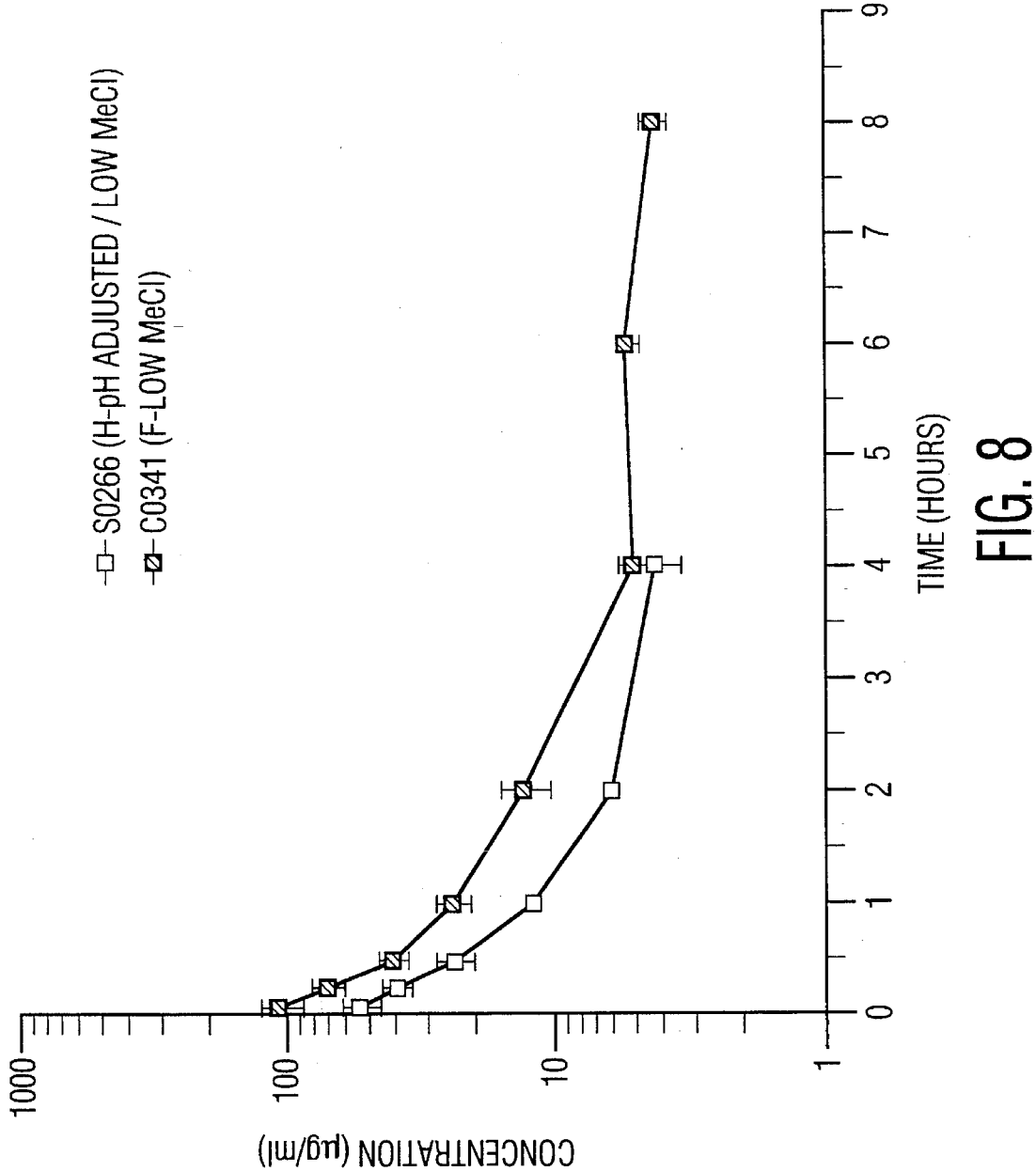
FIG. 8. Free Gentamicjn Plasma Concentrations.
Figure 9:
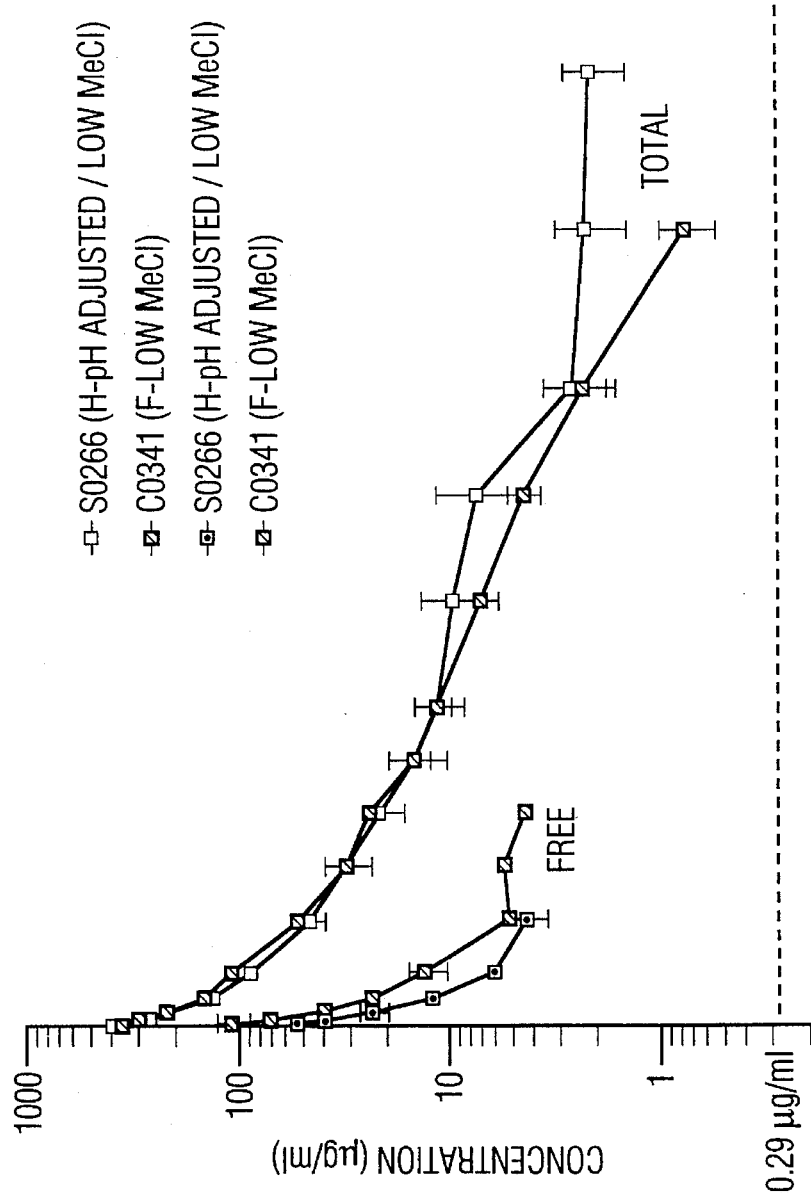
FIG. 9. Total and Free Gentamicin Plasma Concentrations.
Figure 10:
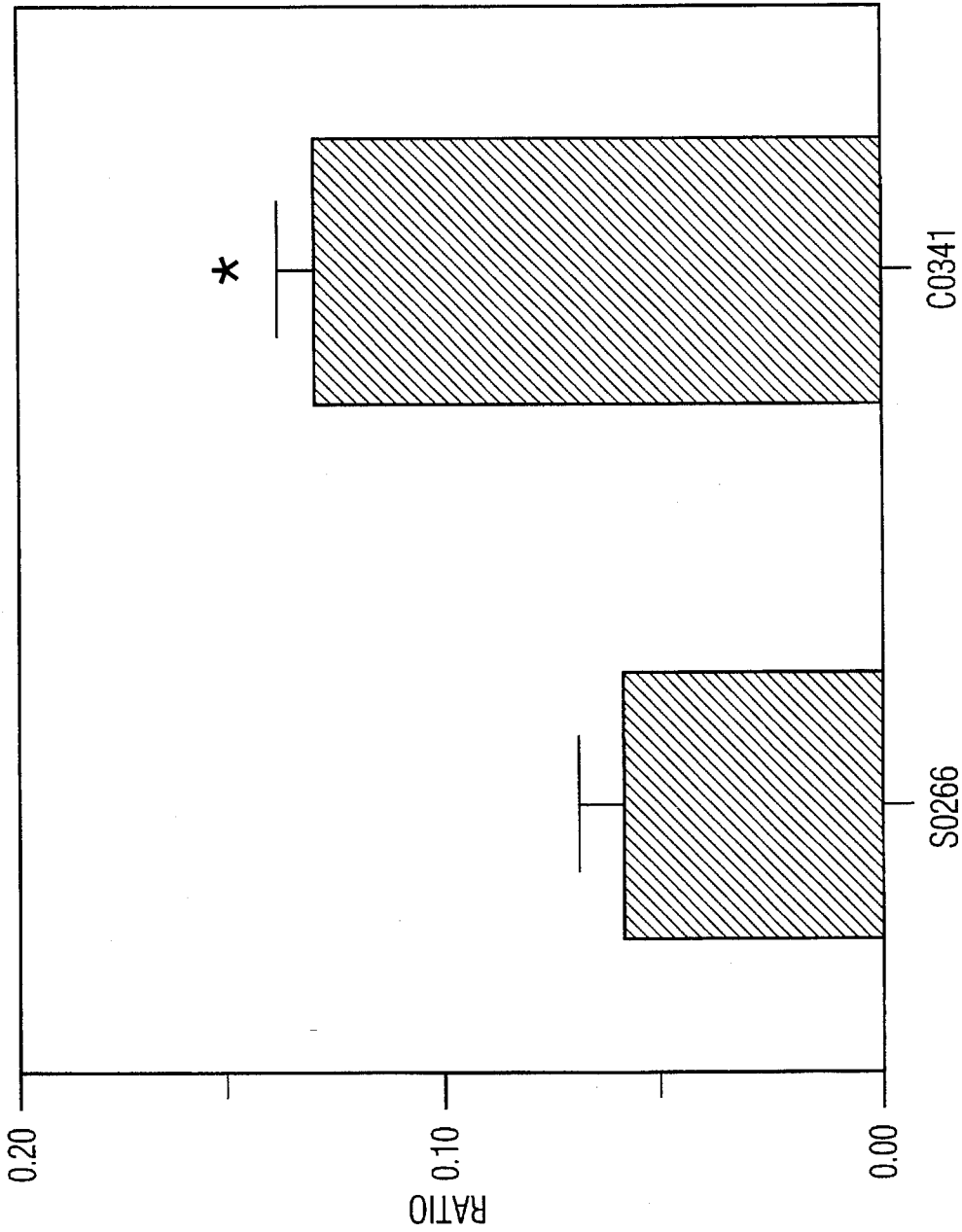
FIG. 10. AUC Ratio (fee/Total) of pH-Adjusted vs. Lower pH Formulations.
Figure 11:
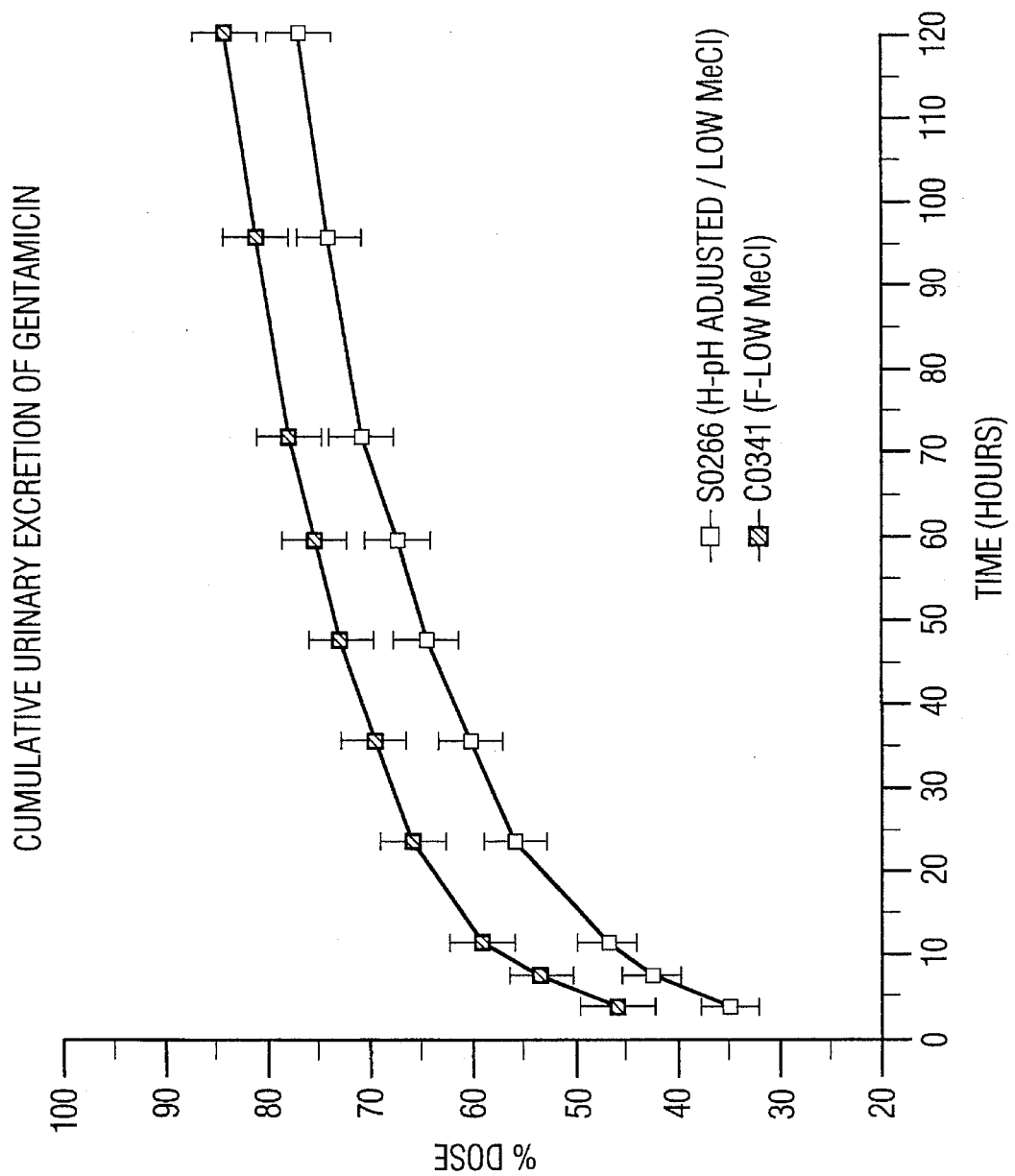
FIG. 11. Cumulative Urinary Excretion of Gentamicin.

FIGS. 4–6 each show a population of liposomes having a single-modal population distribution where substantially all of the liposomes have a particle size within a continuous range of particle sizes. For example, FIG. 4 shows a single-modal population distribution having particle sizes in the range from about 38.4 to 786 nm with the vast majority of liposomes having particle sizes equal to or similar to the mean particle size of 204 nm.

FIGS. 5 and 6 are consistent with the results shown in FIG. 4. FIG. 5 shows a single-modal liposome population distribution in the range of from 53.9 to 583 nm with a mean particle size of 208 nm. FIG. 6 shows a single-modal liposome population distribution in the range of 25 to 1553 nm with a mean particle size of 250 nm.

As shown by FIGS. 4–6, substantially all of the liposomes are within a single-modal population distribution encompassing the desired mean particle size. Most of the liposomes, as shown by the relative intensity values, have the same or similar particle size as the desired mean particle size.

Example 17

14.0 grams of egg phosphatidylcholine (EPC) was dissolved in 30 ml of methylene chloride to form the organic phase. The solution was placed in a reactor vessel of the type shown in FIG. 1 and the mixing assembly rotated at 200 rpm.

8.18 g of gentamicin sulfate was dissolved in 150 ml of a 0.9% saline solution. The resulting solution was added to the reactor vessel under a continuous mixing rate of 200 rpm. The amount of lipid in the reaction mixture was 778 mg/ml and the solvent to aqueous volume ratio was 0.2:1. The pH of the combined phases was 4.4.

Hot water was supplied to the heating jacket 44 to raise the temperature of the contents of the reactor vessel to 35° C.

The heated reaction mixture was then sparged with nitrogen gas at the rate of about 1.0 L/min. In less than two

TABLE 4

| EXAMPLE | MIX SPEED (RPM) | INERT FLOW RATE L/min | REACTION TEMPERATURE Degree C. | PREDICTED MEAN PARTICLE SIZE nm | ACTUAL MEAN PARTICLE SIZE** nm |
| --- | --- | --- | --- | --- | --- |
| 9 | 1000 | 0.04 | 30.0 | 243.76 | 251 |
| 10 | 2000 | 0.04 | 30.0 | 226.78 | 225 |
| 11 | 1000 | 0.80 | 30.0 | 2,884.07 | 2797 |
| 12 | 2000 | 0.80 | 30.0 | 248.66 | 266 |
| 13 | 1000 | 0.04 | 50.0 | 209.26 | 204 |
| 14 | 2000 | 0.04 | 50.0 | 203.86 | 208 |
| 15 | 1000 | 0.80 | 50.0 | 2,641.65 | 2635 |
| 16 | 2000 | 0.80 | 50.0 | 238.50 | 250 |

*Measured by the speed of rotation of the shaft;
**the sum of the diameters of each liposome divided by the total number of liposomes As shown in Table 4, the predicted mean particle size for each of Examples 9–16 closely correlated to the actual mean particle size. The test data shows that the present invention is a reliable method of obtaining a liposome population which corresponds to the preselected mean particle size.

The size distribution of the populations of liposomes produced in accordance with Examples 13, 14 and 16 were determined using the particle size measuring instruments referred to in Examples 1–8. The results are shown in FIGS. 4–6, respectively.

minutes a viscous gel was formed having an appearance, when viewed under a microscope, similar to that shown in the FIG. 3 micrograph. The process was continued until the methylene chloride content was reduced to a level of no more than 0.1% by volume and liposomes formed.

The resulting liposomes were tested for stability by measuring the amount of gentamicin which leaked from the aqueous compartment while being stored at 5° C. The results are shown in Table 5. The "% PURITY" means the average amount of the gentamicin which remained in the liposomes for the given period of time.

TABLE 5

| EXAMPLE | pH | SOLVENT: AQUEOUS VOLUME RATIO | 100 DAYS % PURITY | 200 DAYS % PURITY |
|---|---|---|---|---|
| 17 | 4.4 | 0.2:1 | 91% | 91% |
| 18 | 6.5 | 0.2:1 | 96% | 96% |

Example 18

The procedure of Example 17 was repeated except that the pH of the combined organic and aqueous phases was increased to 6.5 by the addition of 5 ml of 1N sodium hydroxide. The stability of the resulting liposomes was tested in the same manner as in Example 17 and the results are also shown in Table 5.

As shown in Table 5, the use of lower amounts of solvent, 0.2:1 solvent to aqueous ratio, provides liposomes with excellent stability. Example 17 showed a 91% purity after 200 days. When the pH was raised to a level more compatible with the lipid material, the product exhibited an even greater stability, represented by a 96% purity after 200 days.

Examples 19–25

The process of Example 17 was repeated except that changes were made to the solvent to aqueous ratio as shown in Table 6. The amount of gentamicin in the liposomes was measured and the results shown in Table 6.

TABLE 6

| EXAMPLE | SOLVENT:AQUEOUS RATIO | % GENTAMICIN REMAINING IN PRODUCT* |
|---|---|---|
| 19 | 1.00:1 | 16.7 |
| 20 | 0.67:1 | 24.0 |
| 21 | 0.47:1 | 23.6 |
| 22 | 0.33:1 | 24.2 |
| 23 | 0.27:1 | 22.8 |
| 24 | 0.20:1 | 18.3 |
| 25 | 0.13:1 | 10.4 |

*Determined by dividing the total amount of gentamicin in the final product by the amount of gentamicin initially added.

As shown in Table 6, the amount of gentamicin which remained in the liposomes was statistically similar and provided a product which meets general product specifications. At a solvent:aqueous ratio of 0.13:1, a liposome product formed, but the quantity of the gentamicin which remained in the product was lower.

Example 26

The efficacy of a gel-associated composition in preventing surgical wound infections can be determined by the following protocol in which the composition is evaluated for its effect on the normal wound-healing repair process.

All procedures are conducted in clean treatment rooms using surgical instruments, drapes and gloves. The animal models which may be utilized are either guinea pigs or rabbits inoculated with a virulent bacterial strain through a surgical incision on the back. Alternatively, the animal model may utilize immunosuppressed mice, depending upon the outcome of the studies on healthy guinea pigs or rabbits. The present tests were conducted using guinea pigs.

Test samples were prepared from the gel-associated preparation obtained by terminating the procedure set forth in Example 17 upon formation of the viscous gel. As a control, an unloaded gel-associated preparation was also tested.

The guinea pigs were prepared for surgery by shaving the hair on the back and removing the stubble with depilatory cream, after which the exposed skin was washed with soap and water, wiped thoroughly with Betadine® solution, and finally wiped with isopropyl alcohol. The animals were then anesthetized with Metofane® (methoxyflurane) throughout the prepping process.

Two incisions, 2 cm in length each, were made on each side of the midline within the shaved area of each guinea pig's back. The incisions were carried down to, but not through, the fascia, and were extended laterally to create a pouch that was approximately 2 cm×2 cm square. Each treatment was performed in duplicate, and placement of the pouch was duplicated on both sides of the animal.

The animals were inoculated with a bacterial suspension of common surgical wound isolates, the primary bacterial strain being Staphylococcus aureus, but may include Pseudomonas aeruginosa and/or Escherichia coli. The drug sample was tested by two alternative procedures. In one procedure, direct inoculation was followed by immediate application of the drug sample. After inoculation, the wounds were closed.

The animal and the wounds were observed daily. If the animal showed signs of undue stress, they were sacrificed immediately. Seven days after surgery, the animals were sacrificed in a carbon dioxide chamber. Each wound was examined for visual signs of wound infection, and tissue samples were removed for quantitative bacterial counts. Additional tissue samples were removed for histological analysis of the repair tissue. In each case, the treated wounds were compared with those of untreated control animals, those treated with non-gentamicin containing viscous gel and those treated with gel-associated gentamicin.

Example 27

The stability of the liposomal formulations was tested as follows. Liposomes containing gentamicin were prepared as described above, at a gentamicin concentration of 4.5–6.75 mg/ml and a total phospholipid concentration of about 40–60 mg/ml. All components of the liposomal formulations met current U.S.P. requirements. The formulations were tested for sterility and pyrogen content and met current U.S.P. requirements. Residual solvent (methylene chloride) in the preparation was originally about 0.0078% (v/v). The formulations were examined after preparation or, stored in a 5 degrees C upright refrigerator and examined at various intervals of time (days) after preparation. The following criteria of the liposomal formulations were examined: osmolarity (mmole/kg); formulation pH (about 6.5); appearance (conformity to white to off-white opaque dispersion specification); peroxide content (mEq/kg); particle size (microns); free (unentrapped) gentamicin (% of gentamicin available); egg phosphatidylcholine (EPC) purity; head space oxygen content (% oxygen in headspace, empty space, of vial containing liposomal formulation); lipid integrity (% of total phospholipid as hydrolyzed product or non-EPC lipid). Results are presented in Tables 7, 8, 9, 10, 11, 12, 13, 14, 15 and 16 (see below); each table presents data obtained from a distinct lot of liposomes, that is, liposomes prepared under the same specifications and conditions, but at different times. Tables 17, 18, 19 and 20 present criteria for liposomes prepared under the same conditions, but in which the formulation pH was about 4.5.

TABLE 7

PART A

| Interval | | Particle Size (microns) | | | % Free |
|---|---|---|---|---|---|
| (days) | Formulation pH | <1.2 | 1.2–9.6 | >9.6 | Gentamicin |
| 0 | 6.4 | 0 | 98.1 | 1.9 | 12.7 |
| 189–245 | 6.6 | 1.5 | 98.0 | 0 | 8.1 |
| 397–413 | 6.6 | 3.3 | 97 | 0 | 13 |
| 554–565 | 6.5 | 0 | 100 | 0 | 10.1 |
| 743–783 | 6.5 | 1.0 | 99.0 | 0 | 8.2 |

TABLE 7

PART B

| Interval | EPC | Head-space | Lipid Integrity | | | |
|---|---|---|---|---|---|---|
| (days) | Purity (%) | O$_2$ (%) | LysoPC | Sphingo | FFA | Un |
| 0 | 96.5 | 0.5 | 0.4 | 2.9 | ND | ND |
| 189–245 | 98.0 | <0.1 | 0.4 | 1.6 | ND | ND |
| 397–413 | 96 | <0.1 | 0.9 | 2.7 | <1.0 | ND |
| 554–565 | 97 | 0.2 | <0.8 | 3.3 | ND | ND |
| 743–783 | 99.1 | 0.1 | <0.8 | 2.9 | ND | ND |

Lyso PC: lysophosphatidylcholine; sphingo: sphingomyelin; FFA: free fatty acids; un: unknown; ND: not determined.

TABLE 8

PART A

| Interval | | Particle Size (microns) | | | % Free |
|---|---|---|---|---|---|
| (days) | Formulation pH | <1.2 | 1.2–9.6 | >9.6 | Gentamicin |
| 0 | 6.4 | 0 | 98.1 | 1.9 | 12.7 |
| 190–202 | 6.4 | 2 | 98.0 | 0 | 7.2 |
| 390–418 | 6.6 | 3.1 | 96.9 | 0 | 14 |
| 552–560 | 6.6 | 0.9 | 99.1 | 0 | 10.6 |
| 758–772 | 6.6 | 0.0 | 98.1 | 1.9 | 10.9 |

TABLE 8

PART B

| Interval | EPC | Head-space | Lipid Integrity | | | |
|---|---|---|---|---|---|---|
| (days) | Purity (%) | O$_2$ (%) | LysoPC | Sphingo | FFA | Un |
| 0 | 96.5 | 0.5 | 0.4 | 2.9 | ND | ND |
| 190–202 | 93 | 2.9 | 2.8 | 2.4 | 1.7 | ND |
| 390–418 | 97 | <0.1 | 0.3 | 2.3 | 0.2 | ND |
| 552–560 | 98 | 0.1 | <0.8 | 1.6 | ND | ND |
| 758–772 | 97 | 0.1 | <1.6 | 3.3 | ND | ND |

TABLE 9

PART A

| Interval | | Particle Size (microns) | | | % Free |
|---|---|---|---|---|---|
| (days) | Formulation pH | <1.2 | 1.2–9.6 | 9.6 | Gentamicin |
| 0 | | 0 | 98.1 | 1.9 | 12.7 |
| 189–245 | | 2.3 | 98 | 0 | 8.4 |
| 406–427 | | — | 97 | 0 | 11 |
| 554–565 | | 0.1 | 99.9 | 0 | 9.4 |
| 743–783 | | 0.2 | 99.8 | 0 | 7.7 |

TABLE 9

PART B

| Interval | EPC | Head-space | Lipid Integrity | | | |
|---|---|---|---|---|---|---|
| (days) | Purity (%) | O$_2$ (%) | LysoPC | Sphingo | FFA | Un |
| 0 | 96.5 | 0.5 | 0.4 | 2.9 | ND | ND |
| 189–245 | 98 | 0.2 | 0.4 | 1.6 | ND | — |
| 406–427 | 96 | 0.17 | 0.9 | 2.7 | <1.0 | ND |
| 554–565 | 98 | <0.1 | <0.8 | 2.4 | ND | ND |
| 743–783 | 97 | <0.1 | <0.8 | 2.8 | ND | ND |

TABLE 10

PART A

| Interval | | Particle Size (microns) | | | % Free |
|---|---|---|---|---|---|
| (days) | Formulation pH | <1.2 | 1.2–9.6 | >9.6 | Gentamicin |
| 0 | 6.4 | 0 | 98.1 | 1.9 | 12.7 |
| 194–201 | 6.4 | 3 | 97 | 0 | 7.1 |
| 400–451 | 6.4 | 2.6 | 97.4 | 0 | 15 |
| 548–558 | 6.5 | 0.9 | 99.1 | 0 | 10.1 |
| 746–761 | 6.7 | 0.1 | 99.4 | 0.5 | 11.6 |

TABLE 10

PART B

| Interval | EPC | Head-space | Lipid Integrity | | | |
|---|---|---|---|---|---|---|
| (days) | Purity (%) | O$_2$ (%) | LysoPC | Sphingo | FFA | Un |
| 0 | 96.5 | 0.5 | 0.4 | 2.9 | ND | ND |
| 194–201 | 96 | 0.8 | 0.4 | 3.2 | 0.4 | — |
| 400–451 | 975 | 0.8 | 0.8 | 3.2 | ND | ND |
| 548–561 | 97 | <0.1 | <0.8 | 3.2 | ND | ND |
| 746–761 | 98 | <0.1 | <1.6 | 2.5 | ND | ND |

TABLE 11

PART A

| Interval | | Particle Size (microns) | | | % Free |
|---|---|---|---|---|---|
| (days) | Formulation pH | <1.2 | 1.2–9.6 | >9.6 | Gentamicin |
| 0 | 6.4 | 0 | 98.1 | 1.9 | 12.7 |
| 194–201 | 6.4 | 2 | 98 | 0 | 7 |
| 400–451 | 6.5 | 2.5 | 97.54 | 0 | 13.3 |
| 548–561 | 6.7 | 1.3 | 98.7 | 0 | 10.4 |
| 746–763 | 6.7 | 10.0 | 15.4 | 84.6 | 12.2 |

TABLE 11

PART B

| Interval (days) | EPC Purity (%) | Head-space O₂ (%) | Lipid Integrity LysoPC | Sphingo | FFA | Un |
|---|---|---|---|---|---|---|
| 0 | 96.5 | 0.5 | 0.4 | 2.9 | ND | ND |
| 194–201 | 96 | 0.8 | 0.4 | 3.2 | 0.4 | ND |
| 400–451 | 97 | 0.8 | <0.8 | 2.4 | ND | ND |
| 548–561 | 97 | <0.1 | <0.8 | 3.1 | ND | ND |
| 746–763 | 98 | <0.1 | <1.6 | 2.5 | ND | ND |

TABLE 12

PART A

| Interval (days) | Formulation pH | Particle Size (microns) <1.2 | 1.2–9.6 | >9.6 | % Free Gentamicin |
|---|---|---|---|---|---|
| 0 | 6.4 | 0 | 98.1 | 1.9 | 12.7 |
| 189–245 | 6.6 | 1.9 | 98.0 | 0 | 7.4 |
| 397–427 | 6.7 | 2.7 | 97.0 | 0 | 9.4 |
| 554–565 | 6.5 | 0.3 | 99.7 | 0 | 10.1 |
| 743–783 | 6.4 | 0.9 | 99.1 | 0.0 | 8.8 |

TABLE 12

PART B

| Interval (days) | EPC Purity (%) | Head-space O₂ (%) | Lipid Integrity LysoPC | Sphingo | FFA | Un |
|---|---|---|---|---|---|---|
| 0 | 96.5 | 0.5 | 0.4 | 2.9 | ND | ND |
| 189–245 | 98 | 0.1 | 0.4 | 1.6 | ND | — |
| 397–427 | 97 | 0.1 | 0.9 | 2.7 | ND | ND |
| 554–565 | 99.7 | <0.1 | <0.8 | 2.4 | ND | ND |
| 743–783 | 99.1 | <0.1 | <0.8 | 2.9 | ND | ND |

TABLE 13

PART A

| Interval (days) | Formulation pH | Particle Size (microns) <1.2 | 1.2–9.6 | >9.6 | % Free Gentamicin |
|---|---|---|---|---|---|
| 0 | 6.4 | 0 | 98.1 | 1.9 | 12.7 |
| 189–245 | 6.6 | 0. | 99.8 | 0 | 6.4 |
| 397–427 | 6.7 | 2.5 | 91 | 6.2 | 9.6 |
| 554–568 | 6.5 | 0 | 99.9 | 0.1 | 9.2 |
| 743–783 | 6.3 | 1.0 | 99.0 | 0 | 8.8 |

TABLE 13

PART B

| Interval (days) | EPC Purity (%) | Head-space O₂ (%) | Lipid Integrity LysoPC | Sphingo | FFA | Un |
|---|---|---|---|---|---|---|
| 0 | 98.5 | 0.5 | 0.4 | 2.9 | ND | ND |
| 189–245 | 98 | 0.4 | 0.4 | 1.6 | <0.9 | — |
| 397–427 | 96 | 0.2 | 0.9 | 2.7 | <1.0 | ND |
| 554–565 | 97 | 0.1 | <0.8 | 3.3 | ND | ND |
| 743–783 | 97.1 | 0.1 | <0.8 | 2.9 | ND | ND |

TABLE 14

PART A

| Interval (days) | Formulation pH | Particle Size (microns) <1.2 | 1.2–9.6 | >9.6 | % Free Gentamicin |
|---|---|---|---|---|---|
| 0 | 6.4 | 0 | 98.1 | 1.9 | 12.7 |
| 190–202 | 6.4 | 2 | 98 | 0 | 7.4 |
| 390–451 | 6.6 | 2.4 | 97.6 | 0 | 9.4 |
| 552–564 | 6.6 | 0.7 | 99.3 | 0 | 10.1 |
| 758–773 | 6.6 | 0.1 | 99.0 | 0 | 8.8 |

TABLE 14

PART B

| Interval (days) | EPC Purity (%) | Head-space O₂ (%) | Lipid Integrity LysoPC | Sphingo | FFA | Un |
|---|---|---|---|---|---|---|
| 0 | 96.5 | 0.5 | 0.4 | 2.9 | ND | ND |
| 190–202 | 93 | 4.4 | 2.8 | 2.4 | 1.7 | ND |
| 390–451 | 97 | 0.16 | 0.3 | 2.3 | 0.2 | ND |
| 552–564 | 98 | 0.2 | <0.8 | 2.4 | ND | ND |
| 758–773 | 98 | 0.3 | <1.6 | 2.5 | ND | ND |

TABLE 15

PART A

| Interval (days) | Formulation pH | Particle Size (microns) <1.2 | 1.2–9.6 | >9.6 | % Free Gentamicin |
|---|---|---|---|---|---|
| 0 | 6.4 | 0.0 | 98.1 | 1.9 | 12.7 |
| 189–245 | 6.6 | 1.5. | 97 | 0 | 6.6 |
| 397–413 | 6.6 | 2.8 | 91 | 0 | 13 |
| 559–568 | 6.5 | 0.0 | 98.2 | 1.8 | 11.1 |
| 743–784 | 6.5 | 0.7 | 99.3 | 0 | 11.8 |

TABLE 15

PART B

| Interval (days) | EPC Purity (%) | Head-space O₂ (%) | Lipid Integrity LysoPC | Sphingo | FFA | Un |
|---|---|---|---|---|---|---|
| 0 | 96.5 | 0.5 | 0.4 | 2.9 | ND | ND |
| 189–245 | 98 | 0.4 | 0.4 | 1.6 | ND | — |
| 397–413 | 96 | 0.2 | 0.9 | 2.7 | ND | ND |
| 559–568 | 97 | 0.2 | <0.8 | 3.3 | ND | ND |
| 743–784 | 98 | 0.3 | <0.8 | 2.0 | <0.8 | ND |

TABLE 16

PART A

| Interval (days) | Formulation pH | Particle Size (microns) <1.2 | 1.2–9.6 | >9.6 | % Free Gentamicin |
|---|---|---|---|---|---|
| 0 | 6.42 | 0 | 98.1 | 1.9 | 12.7 |
| 190–201 | 6.9 | 2 | 94 | 0 | 9.5 |
| 390–417 | 6.3 | 2 | 98 | 0.1 | 1.1 |
| 552–560 | 6.6 | 0.2 | 99.8 | 0.0 | 13.9 |
| 758–772 | 6.6 | 0.3 | 99.7 | 0.0 | 17.6 |

TABLE 16

PART B

| Interval (days) | EPC Purity (%) | Head-space O$_2$ (%) | Lipid Integrity | | | |
|---|---|---|---|---|---|---|
| | | | LysoPC | Sphingo | FFA | Un |
| 0 | 96.5 | 0.5 | 0.4 | 2.9 | ND | ND |
| 190–201 | 93 | 3.6 | 2.8 | 2.4 | 1.7 | ND |
| 390–417 | 97 | 0.2 | 0.5 | 2.3 | ND | ND |
| 552–560 | 98 | 0.15 | <0.8 | 2.4 | ND | ND |
| 758–772 | 98 | 0.1 | <1.6 | 2.5 | ND | ND |

TABLE 17

PART A

| Interval (days) | Formulation pH | Particle Size (microns) | | | % Free Gentamicin |
|---|---|---|---|---|---|
| | | <1.2 | 1.2–9.6 | >9.6 | |
| 0 | 4.6 | 5.9 | 94.1 | 0 | 6.1 |
| 189–192 | 4.4 | 7.4 | 92.6 | 0 | 4.5 |
| 375–382 | 4.5 | 8.0 | 92.0 | 0.7 | 4.5 |
| 556–573 | 4.6 | 5.5 | 94.5 | 0 | 61 |
| 745–773 | 4.6 | 4.1 | 94.7 | 1.2 | 5.6 |

TABLE 17

PART B

| Interval (days) | EPC Purity (%) | Head-space O$_2$ (%) | Lipid Integrity | | | |
|---|---|---|---|---|---|---|
| | | | LysoPC | Sphingo | FFA | Un |
| 0 | 95.9 | 1.7 | 0.5 | 3.1 | 0.5 | — |
| 189–245 | 93.0 | — | 1.7 | 2.7 | 2.7 | ND |
| 397–427 | 96.0 | — | 1.3 | 2.7 | <0.4 | ND |
| 554–565 | 92 | — | 4.0 | 2.0 | 1.9 | ND |
| 743–783 | 88 | <0.1 | 6.7 | 2.1 | 3.3 | ND |

TABLE 18

PART A

| Interval (days) | Formulation pH | Particle Size (microns) | | | % Free Gentamicin |
|---|---|---|---|---|---|
| | | <1.2 | 1.2–9.6 | >9.6 | |
| 0 | 4.6 | 5.9 | 94.1 | 1.9 | 6.1 |
| 374–383 | 4.5 | 9.0 | 91.0 | 0 | 4.1 |
| 551–579 | 4.6 | 4.7 | 95.1 | 0.2 | 5.9 |
| 752–787 | 4.7 | 2.8 | 97.2 | 0 | 5.6 |

TABLE 18

PART B

| Interval (days) | EPC Purity (%) | Head-space O$_2$ (%) | Lipid Integrity | | | |
|---|---|---|---|---|---|---|
| | | | LysoPC | Sphingo | FFA | Un |
| 0 | 95.9 | 1.7 | 0.5 | 3.1 | 0.5 | — |
| 374–383 | 90.0 | — | 4.0 | 3.4 | 2.1 | ND |
| 551–579 | 85.0 | — | 9.1 | 3.3 | 2.5 | ND |
| 752–787 | 87.0 | <0.1 | 6.7 | 2.8 | 4.0 | ND |

TABLE 19

PART A

| Interval (days) | Formulation pH | Particle Size (microns) | | | % Free Gentamicin |
|---|---|---|---|---|---|
| | | <1.2 | 1.2–9.6 | >9.6 | |
| 0 | 4.4 | 7.9 | 91.7 | 0.4 | 10.7 |
| 114–151 | 4.5 | 7.5 | 91.9 | 0.6 | 10.8 |
| 224–234 | 4.4 | 7.5 | 91.5 | 1.0 | 10.6 |
| 558–560 | 4.5 | 7.9 | 92.0 | 0.6 | 8.7 |
| 780–815 | 4.5 | 6.4 | 92.1 | 1.5 | 11.1 |

TABLE 19

PART B

| Interval (days) | EPC Purity (%) | Head-space O$_2$ (%) | Lipid Integrity | | | |
|---|---|---|---|---|---|---|
| | | | LysoPC | Sphingo | FFA | Un |
| 0 | 94.8 | 0.4 | 0.9 | 3.6 | 0.6 | ND |
| 114–151 | 90.8 | — | 2.3 | 3.6 | 2.4 | — |
| 224–234 | 90.9 | 0.28 | 2.0 | 4.4 | 2.1 | ND |
| 558–560 | 88 | — | 5.3 | 2.4 | 4.1 | — |
| 780–815 | 82.4 | 0.8 | 8.3 | 2.3 | 6.1 | ND |

TABLE 20

PART A

| Interval (days) | Formulation pH | Particle Size (microns) | | | % Free Gentamicin |
|---|---|---|---|---|---|
| | | <1.2 | 1.2–9. | >9.6 | |
| 0 | 4.4 | 7.9 | 91.7 | 0.4 | 10.7 |
| 118–155 | 4.4 | 7.7 | 91.6 | 0.7 | 10.8 |
| 228–238 | 4.5 | 8.9 | 89.9 | 1.2 | 11.0 |
| 562–564 | 4.7 | 8.3 | 91.0 | 0.4 | 8.6 |
| 787–819 | 4.6 | 8.0 | 91.4 | 0.6 | 11.1 |

TABLE 20

PART B

| Interval (days) | EPC Purity (%) | Head-space O$_2$ (%) | Lipid Integrity | | | |
|---|---|---|---|---|---|---|
| | | | LysoPC | Sphingo | FFA | Un |
| 0 | 94.8 | 0.4 | 0.9 | 3.6 | 0.6 | ND |
| 118–155 | 90.5 | — | 2.3 | 3.6 | 2.7 | ND |
| 228–238 | 90.3 | 0.31 | 2.0 | 4.4 | 2.5 | ND |
| 562–564 | 89 | — | 4.5 | 2.4 | 3.6 | ND |
| 787–819 | 83.7 | 0.2 | 9.0 | 3.1 | 3.8 | ND |

Example 28

Twenty-three male Sprague-Dawley rats (350–400 g) were randomly assigned to two treatment groups. Each group was treated with a 20 mg/kg i.v. dose of gentamicin (i.v. tail bolus). One group received liposomal gentamicin having a pH of about 4.5 (lower pH formulation; Lot #CO341, 4.8 mg/ml gentamicin and 53.1 mg/ml total phospholipid). The second group received liposomal gentamicin having a pH of about 6.5 (higher pH formulation; Lot No. S0266, 6.0 mg/ml gentamicin and 43.7 mg/ml total phospholipid).

Apparatus and reagents used, drug administration and sample collection, gentamicin assay and pharmacokinetic evaluation were as follows:

1.1 Apparatus & Reagents 1.1.1 TDx Analyzer (Serial #17734, Abbott Laboratories, Chicago, IL)
1.1.2 TDx Gentamicin Assay Kits, Controls, Calibrators and Buffers obtained from Abbott Laboratories, Chicago, IL).
1.1.3 Pentobarbital Sodium (Fort Dodge Laboratories, INC. Fort Dodge, Iowa)
1.1.4 Centricon-30 Microconcentrator (30,000 MW cut-off) product #4209 AMICON Corporation Scientific System Division, Danvers, MA.

1.2. Drug Administration and Sample Collection

Prior to drug administration, baseline plasma and urine samples were collected from each rat. A 20 mg/kg intravenous (tail vein) bolus dose of G-65 Low Methylene Chloride Formulation (Lot #CO341) was administered to one group of rats (Group B) while the second group (Group B) received a similar dose of G-65 pH Adjusted Formulation (Lot #S0266).

Following drug administration in each rat, 100 to 500 µl of blood were drawn using citrate flushed 1 cc syringes at 0.083, 0.25, 1.00, 2.00 4.00, 6.00, 8.00, 10.00, 12.00, 16.00, 20.00, 24.00, 36.00 and 48.00 hr. The collected blood samples were centrifuged in the micro centrifuge for 2 minutes. The plasma was collected and processed to determine total and free gentamicin as described in Section 1.3.

After rinsing the metabolism cages with TDx Dilution Buffer, the urine excreted by each rat was collected at 4.00, 8.00, 12.00, 24.00, 36.00, 48.00, 60.00, 72.00, 96.00 and 120 hr. The volume of urine collected was recorded for each rat and period of collection. The urine samples were centrifuged for five minutes to remove particulate debris. The urine samples were then assayed to determine gentamicin concentration as described in Section 1.3.

At the end of sample collection, animals were euthanized with carbon dioxide (dry ice).

1.3. Gentamicin Assay

The concentration of gentamicin in plasma and urine samples were determined using a fluorescence polarization immunoassay technique on the TDx system (Abbott Diagnostic Laboratories) as described in Biological Sciences Report G65-009.

1.4 Pharmacokinetic Evaluation:

The pharmacokinetics of gentamicin were determine by use of model-independent methods. Parameters were determine from area under the plasma concentration-time curves (AUC) and their first moment (AUMC) estimated by trapezoidal methods. The elimination half-life ($t\frac{1}{2}\beta$), mean residence time (MRT), total body clearance (Clt), and volume of distribution at steady state (Vss) were estimated from the following relationships:

$t\frac{1}{2}\beta = 0.693/\beta$

MRT=AUMC/AUC

Clt=Dose/AUC

Vss=Dose(AUMC)/(AUC)$^2$

Cumulative gentamicin urinary excretion and excretion rate at each mid point of collection time were used in evaluating gentamicin disposition from the urinary data. Renal clearance (Clr) and elimination half-life ($t\frac{1}{2}\beta$) were calculated from the following relationships:

Clr=XU$^\infty$/AUC $t\frac{1}{2}\beta = 0.693/\beta$

Where XU$^\infty$ is the amount of urine excreted at infinity which was estimated from:

$$XU^\infty = XU^{120} + \frac{dxu/dt}{\beta}$$

Where XU$^{120}$ is the cumulative urinary excretion for the 5 days, dxu/dt is the excretion rate at 120 hours, and β the terminal slope of log dxu/dt versus time at midpoint of excretion.

General Linear Model (SAS Institute Inc., N.C.) was used in determining differences in gentamicin pharmacokinetic parameters between the two treatment groups.

Following drug administration, serial :blood (baseline, 0.083, 0.25.50, 1, 2, 4, 6, 8, 10, 12, 16, 20, 24, 30, 36 and 48 hours) and urine samples (baseline, 4, 8, 12, 24, 36, 48, 60, 72, 96 and 120 hours) were determined using fluorescence polarization immunoassay (TDx, Abbor Labs.). Results are presented in Tables 21, 22, 23 and 24, and FIGS. 7–13.

Plasma concentrations were used to estimate mean pharmacokinetic parameters for total and free gentamicin. For the lower pH formulation, AUC, Clt and Vss were 795.34+/−278.78 micrograms-hr/ml, 27.80+/−8.65 ml/hr/kg and 0.110+/−0.035 l/kg, respectively, as compared to 809.02+/−377.25 micrograms-hr/ml, 29.39+/−12.15 ml/hr/kg and 0.132 +/−0.029 l/kg, respectively, for the higher pH formulation. The MRT and T ½ of total gentamicin in the higher pH group were longer (P<0.05) than those in the lower pH group (4.79+/−1.39 hr and 5.04+/−1.91 h, vs. 3.72 +/−0.79 hr and 4.10+/−1.15 hr, respectively). The free gentamicin fraction was larger in the lower pH group with the Cmax and AUClast values of 115.67+/−51.42 micrograms/ml and 90.842+/−51.42 micrograms-hr/ml, respectively, compared to 57.31 and 29.00 micrograms/ml and 44.39+/−6.778 micrograms-hr/ml, respectively, for the higher pH group. The percentages of the administered gentamicin excreted in urine were 81.58+/−10.96 and 76.16+/−11.81, respectively, for the lower and higher pH groups. The terminal excretion rate (β) was significantly lower for the higher pH treatment group (0.017+/−0.004/hr, vs. 0.021+/−0.005/hr, respectively for the higher and lower pH formulations), which also had a corresponding longer half-life (43.31+/−13.26 hr, vs. 35.11+/−9.96 hr, respectively, for the higher and lower pH groups).

TABLE 21

Plasma pharmacokinetics of Total Gentamicin of pH adjusted and Low MeCl G-65 Formulations in Rats

| Parameter | G-65 H formulation (Lot # SO266) (N = 11) | G-65 F-formulation (Lot # CO341) (N = 12) |
|---|---|---|
| T½α (hr) | 0.46(0.29) | 0.81(0.31) |
| T½β (hr) | 3.00(0.81) | 3.32(0.42) |
| Vc (l/kg) | 0.042(0.01) | 0.042(0.01) |
| Vp (l/kg) | 0.077(0.03) | 0.041(0.01) |
| Vss (l/kg) | 0.092(0.01) | 0.092(0.010) |
| Clc (ml/hr/kg) | 0.139(0.047) | 0.68(0.025) |
| Clt (ml/hr/kg) | 0.033(0.004) | 0.029(0.003) |

Values expressed as Means (SEM)

Formulae:
T½=0.693/α
T½β=0.693/β
Vc=Dose/(A+B)
Vp=Vc(K12/K21)
Vss=Vc+Vp
Clc=VcK12

$Clt=Vc\beta$

TABLE 22

Plasma pharmacokinetics of Total Gentamicin of
pH adjusted and Low MeCl G-65 Formulations in Rats

| Parameter | G-65 H formulation (Lot # SO266) (N = 11) | G-65 F-formulation (Lot # CO341) (N = 12) |
|---|---|---|
| AUC(Ug-hr/Ml) | 809.02(99.31) | 795.34(95.08) |
| T½ (hr) | 4.79(.34) | 3.72(.32)* |
| MRT (hr) | 5.04(.47) | 4.10(4.5) |
| Clt (ml/hr/kg) | 29.39(3.15) | 27.80(3.02) |
| Vss (l/kg) | .132(.010) | .110(.010) |

Values expressed as Means (SEM)
*Significantly different from pH adjusted G-65 formulation (P < .05)

Formulae:
T½=0.693/β
MRT=AUMC/AUC
Clt=Dose/AUC
Vss=Dose(AUMC)/(AUC*AUC)

TABLE 23

Plasma pharmacokinetics of Free Gentamicin of
pH adjusted and Low MeCl G-65 Formulations in Rats

| Parameter | G-65 H formulation (Lot # SO266) (N = 9) | G-65 F-formulation (Lot # CO341) (N = 11) |
|---|---|---|
| AUC(Ug-hr/Ml) | 56.78(29.44) | 101.80(34.80)* |
| Cmax (ug/ml) | 57.33(28.97) | 115.67(57.09)* |
| T½ (hr) | 2.22(2.07) | 1.64(0.99) |
| MRT (hr) | 2.66(2.49) | 2.13(1.35) |

Values expressed as Means (SD)
*Significantly different from pH adjusted G-65 formulation (P < .05)

Formulae:
T½=0.693/β
MRT=AUMC/AUC
Cmax=concentration at 0.083 hr

TABLE 24

Urine pharmacokinetics of Gentamicin of
pH adjusted and Low MeCl G-65 Formulations in Rats

| Parameter | G-65 H formulation (Lot # SO266) (N = 11) | G-65 F-formulation (Lot # CO341) (N = 12) |
|---|---|---|
| Dose Excreted (%) | 76.16(3.56) | 81.58(3.16) |
| Clt (mlj/hr/kg) | 33.36(4.32) | 29.08(3.40) |
| Clr (ml/hr/kg) | 25.16(2.84) | 24.26(2.68) |
| T½ (hr) | 35.11(3.00) | 44.49(4.09) |

Values expressed as Means (SD)

Formulae:
T½=0.693/β
Clt=Dose/AUC
Clr=Xuinf/AUC

What is claimed is:

1. A process for producing a multilamellar liposome having a predetermined and selected mean particle size consisting essentially of:
   (a) combining an organic phase comprising a lipid and a water-immiscible organic solvent and an aqueous phase such that the volume ratio of the organic phase to the aqueous phase is less than 3:1; and
   (b) whereby the combined phases are mixed at a speed, temperature and inert gas flow rate that are determined in accordance with Equation (1) and are sufficient to produce multilamellar liposomes having said predetermined mean particle size,
wherein Equation (1) is:

$$y=B_0+B_1X_1+B_2X_2+B_3+X_3+B_{12}X_1X_2+B_{13}X_1X_3+B_{23}X_2X_3+B_{11}X^2_1+B_{22}X^2_2+B_{33}X^2_3$$

and wherein: y=the desired mean particle size of the liposome; $X_1$=the reaction mixing speed; $X_2$=the inert gas flow rate; $X_3$=the temperature of the reaction; $B_0$=a constant; $B_1$=coefficient of regression for the main effect Of the reaction mixing speed; $B_2$=coefficient of regression for the main effect of the inert gas flow rate; $B_3$=coefficient of regression for the main effect of the reaction temperature; $B_{12}$=coefficient of regression of the interaction of mixing speed and inert gas flow rate; $B_{13}$=coefficient of regression of the interaction of mixing speed and reaction temperature; $B_{23}$=coefficient of regression of the interaction of inert gas flow rate and reaction temperature; $B_{11}$=coefficient of regression of the quadratic effect Of mixing; $B_{22}$=coefficient of regression of the quadratic effect of inert gas flow rate; $B_{33}$=coefficient of regression of the quadratic effect of reaction temperature.

2. The process of claim 1, wherein the organic phase to aqueous phase volume ratio is from about 0.2:1 to about 1.0:1.

3. The process of claim 1, comprising adjusting the pH of the combined phases to a level which inhibits degradation of the lipid.

4. The process of claim 3, wherein the pH of the combined phases is from about 5.5 to about 7.5.

5. The process of claim 4, wherein the pH of the combined phases is about 6.5.

6. The multilamellar liposome of claim 1, comprising a solute entrapped in its aqueous compartments, wherein the concentration of the solute entrapped in each of the aqueous compartments of the multilamellar liposome is substantially equal.

7. The process of claim 1, further comprising associating a bioactive agent with the liposome.

8. The process of claim 1, wherein the bioactive agent is an aminoglycoside antibiotic.

9. The process of claim 8, wherein the aminoglycoside antibiotic is selected from the group consisting of gentamicin, streptomycin, dihydrostreptomycin, tobramycin, neomycin B, paromycin, ribostamycin, lividomycin, kanamycin, viomycin, sisomicin, netilmicin and amikacin.

10. The process of claim 9 wherein the aminoglycoside antibiotic is gentamicin.

11. The process of claim 1, wherein the inert gas flow rate is from about 0.4 to about 1.2 liters/min.

12. The process of claim 1, wherein the reaction temperature is from about 20 to about 80° C.

13. The process of claim 1, wherein the mixing speed is in the range of up to about 2,000 rpm.

14. The process of claim 1, further comprising varying the predetermined mean particle size by varying at least one of said process conditions determined in accordance with Equation (1) while holding the remaining process conditions constant.

15. The process of claim 14, comprising varying the inert gas flow rate while holding the mixing speed and reaction temperature constant.

16. The process of claim 15, further comprising varying the inert gas flow rate and the mixing speed while holding the reaction temperature constant.

17. The process of claim 1, wherein the amount of lipid is at least about 10 mg/ml of the combined phases.

* * * * *